United States Patent
Lo et al.

(10) Patent No.: US 10,113,116 B2
(45) Date of Patent: Oct. 30, 2018

(54) LIQUID CRYSTAL COMPOUND AND LIQUID CRYSTAL COMPOSITION EMPLOYING THE SAME

(71) Applicant: DAXIN MATERIALS CORPORATION, Taicgung (TW)

(72) Inventors: Chih-Yuan Lo, Taicgung (TW); Hsin-Cheng Liu, Taicgung (TW); Guo-Yu Lan, Taicgung (TW); Chun-Chih Wang, Taicgung (TW)

(73) Assignee: DAXIN MATERIALS CORPORATION, Taichung (TW)

( * ) Notice: Subject to any disclaimer, the term of this patent is extended or adjusted under 35 U.S.C. 154(b) by 0 days.

(21) Appl. No.: 15/008,194

(22) Filed: Jan. 27, 2016

(65) Prior Publication Data

US 2016/0222295 A1 Aug. 4, 2016

(30) Foreign Application Priority Data

Jan. 30, 2015 (TW) .............................. 104103146 A
May 4, 2015 (TW) .............................. 104114102 A
May 20, 2015 (TW) .............................. 104116024 A

(51) Int. Cl.
*C09K 19/32* (2006.01)
*C09K 19/34* (2006.01)
*C07D 317/46* (2006.01)
*C09K 19/04* (2006.01)

(52) U.S. Cl.
CPC ........ *C09K 19/3405* (2013.01); *C07D 317/46* (2013.01); *C09K 19/32* (2013.01); *C09K 2019/0444* (2013.01); *C09K 2019/0466* (2013.01); *C09K 2019/3408* (2013.01); *C09K 2019/3425* (2013.01); *C09K 2019/3427* (2013.01)

(58) Field of Classification Search
CPC .................................................... C09K 19/32
See application file for complete search history.

(56) References Cited

U.S. PATENT DOCUMENTS

| 8,388,861 B2 | 3/2013 | Wang et al. | |
| 8,574,455 B2* | 11/2013 | Yaguchi | C09K 19/0403 252/299.61 |
| 2012/0132854 A1* | 5/2012 | Wang | C09K 19/32 252/299.61 |

FOREIGN PATENT DOCUMENTS

JP 2003261562 A * 9/2003
TW I462993 B 12/2014

* cited by examiner

*Primary Examiner* — Chanceity N Robinson
(74) *Attorney, Agent, or Firm* — Muncy, Geissler, Olds & Lowe, P.C.

(57) ABSTRACT

A liquid crystal compound and a composition employing the same are provided. The liquid crystal compound has a structure represented by Formula (I)

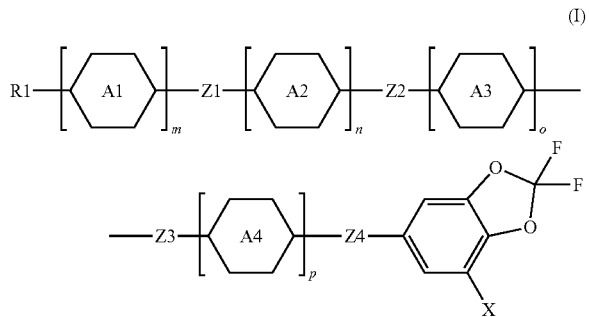

wherein R1, A1, A2, A3, A4, Z1, Z2, Z3, Z4, X, m, n, o, and p are defined as in the description.

16 Claims, No Drawings

LIQUID CRYSTAL COMPOUND AND LIQUID CRYSTAL COMPOSITION EMPLOYING THE SAME

CROSS REFERENCE TO RELATED APPLICATIONS

This Application claims priority of Taiwan Patent Application No. 104103146, filed on Jan. 30, 2015, Taiwan Patent Application No. 104114102, filed on May 4, 2015, and Taiwan Patent Application No. 104116024, filed on May 20, 2015, the entirety of which is incorporated by reference herein.

BACKGROUND

Field of the Disclosure

The present disclosure relates to a liquid crystal compound, and in particular it relates to a liquid crystal compound and a liquid crystal composition.

Description of the Related Art

Liquid crystal displays have become mainstream flat-panel displays because of their small size, light weight, low power consumption, and excellent display quality.

For the liquid crystal material used in the liquid crystal display, high dielectric anisotropy and low viscosity are important. In particular, with high dielectric anisotropy, the liquid crystal display may have a low driving voltage and low energy consumption.

However, the liquid crystal compound having high dielectric anisotropy usually has high viscosity. The response speed of the liquid crystal compound will be reduced due to high viscosity. Therefore, a liquid crystal compound having sufficiently high dielectric anisotropy without incurring high viscosity is needed.

BRIEF SUMMARY

The disclosure provides a liquid crystal compound. The liquid crystal compound has high refractive anisotropy ($\Delta n$), good dielectric anisotropy ($\Delta \varepsilon$), proper rotational viscosity coefficient ($\gamma 1$) and a low ratio of rotational viscosity coefficient to dielectric anisotropy (i.e., $\gamma 1/\Delta \varepsilon$). The disclosure also provides a liquid crystal composition including the liquid crystal compound. Accordingly, the response speed of the liquid crystal material will be significantly increased.

In one aspect, the disclosure provides a liquid crystal compound. The liquid crystal compound is represented by Formula (I):

wherein

R1 represents hydrogen, a $C_1$-$C_{10}$ alkyl group, or a $C_2$-$C_{10}$ alkenyl group, where the $C_1$-$C_{10}$ alkyl group or the $C_2$-$C_{10}$ alkenyl group is unsubstituted or at least one —$CH_2$— of the $C_1$-$C_{10}$ alkyl group or the $C_2$-$C_{10}$ alkenyl group is replaced by —O—, —S—, —O—CO—, —OC—O—, or —O—CO—O—, provided that the —O—, —S—, —O—CO—, —OC—O—, and —O—CO—O— do not directly bond to one another, and/or at least one hydrogen of the $C_1$-$C_{10}$ alkyl group or the $C_2$-$C_{10}$ alkenyl group is substituted by halogen, CN, or $CF_3$;

each of A1, A2, A3, and A4 independently represents a 1,4-phenylene group, a 1,4-cyclohexylene group, a divalent dioxabicyclo[2.2.2]octylene group, a divalent trioxabicyclo[2.2.2]octylene group, or a divalent 2,5-indanylene group, where the 1,4-phenylene group, the 1,4-cyclohexylene group, or the divalent 2,5-indanylene group is unsubstituted or at least one hydrogen of the 1,4-phenylene group, the 1,4-cyclohexylene group, or the divalent 2,5-indanylene group is substituted by halogen, CN, or $CF_3$, and/or at least one —$CH_2$— of the 1,4-cyclohexylene group is replaced by —O—, —S—, —O—CO—, —OC—O—, or —O—CO—O—, provided that the —O—, —S—, —O—CO—, —OC—O—, and —O—CO—O— do not directly bond to one another, and/or at least one —$CH_2$— of the divalent 2,5-indanylene group is replaced by —O— or —S—, provided that the —O— and —S— do not directly bond to one another;

each of Z1, Z2, Z3, and Z4 independently represents a single bond, a $C_1$-$C_4$ alkylene group, a $C_2$-$C_4$ alkenylene group, a $C_2$-$C_4$ alkynylene group, —O—CO—, or —CO—O—, where the C1-C4 alkylene group, the C2-C4 alkenylene group, or the $C_2$-$C_4$ alkynylene group is unsubstituted or at least one hydrogen of the C1-C4 alkylene group, the C2-C4 alkenylene group, or the $C_2$-$C_4$ alkynylene group is substituted by halogen, and/or at least one —$CH_2$— of the C1-C4 alkylene group, the C2-C4 alkenylene group, or the $C_2$-$C_4$ alkynylene group is replaced by —O— or —S—, provided that the —O— and —S- do not directly bond to each other;

X represents hydrogen, halogen, CN. $CF_3$, or $CCl_3$; and each of m, n, o, and p independently represents 0 or 1, and m+n+o+p>0.

In other aspects, the disclosure also provides a liquid crystal composition. The liquid crystal composition includes a first component including at least one liquid crystal compound represented by the above Formula (I). The liquid crystal composition also includes a second component including at least one liquid crystal compound represented by Formula (II):

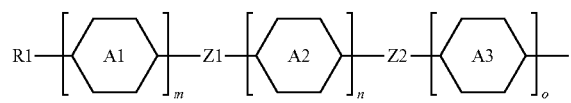 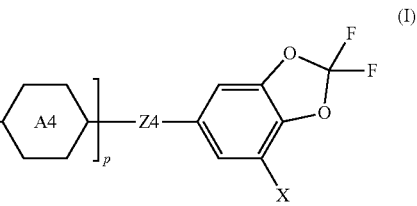

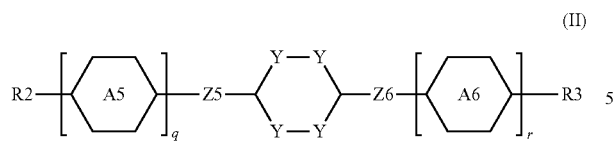

wherein
- R3 represents a $C_1$-$C_{10}$ alkyl group, a $C_2$-$C_{10}$ alkenyl group, halogen, —$CF_3$, —OCH=$CF_2$, or —$OCF_3$;
- R2 represents hydrogen, a $C_1$-$C_{10}$ alkyl group, or a $C_2$-$C_{10}$ alkenyl group, where the $C_1$-$C_{10}$ alkyl group or the $C_2$-$C_{10}$ alkenyl group is unsubstituted or at least one —$CH_2$— of the $C_1$-$C_{10}$ alkyl group or the $C_2$-$C_{10}$ alkenyl group is replaced by —O—, —S—, —CO—, —O—CO—, —CO—O—, or —O—CO—O—, and wherein the —O—, —S—, —CO—, —O—CO—, —CO—O—, and —O—CO—O— do not directly bond to one another, and/or at least one hydrogen of the $C_1$-$C_{10}$ alkyl group or the $C_2$-$C_{10}$ alkenyl group is substituted by halogen, CN, or $CF_3$;
- Y represents —C(R4)$_2$-, —O—, or —S—, and —O— does not directly bond to —O— or —S—, and —S— does not directly bond to —S—, where each of R4 independently represents hydrogen or halogen;
- each of A5 and A6 independently represents a 1,4-phenylene group, a 1,4-cyclohexylene group, a divalent dioxabicyclo[2.2.2]octylene group, a divalent trioxabicyclo[2.2.2]octylene group, or a divalent 2,5-indanylene group, where the 1,4-phenylene group, the 1,4-cyclohexylene group, or the divalent 2,5-indanylene group is unsubstituted or at least one hydrogen of the 1,4-phenylene group, the 1,4-cyclohexylene group, or the divalent 2,5-indanylene group is substituted by halogen or CN, and/or at least one —$CH_2$— of the 1,4-cyclohexylene group is replaced by —O—, —NH—, or —S—, provided that the —O—, —NH—, and —S— do not directly bond to one another, or at least one —$CH_2$— of the divalent 2,5-indanylene group is replaced by —O—, —NH—, or —S—, provided that the —O—, —NH—, and —S— do not directly bond to one another;
- each of Z5 and Z6 independently represents a single bond, a C1-C4 alkylene group, a C2-C4 alkenylene group, a $C_2$-$C_4$ alkynylene group, —CO—O—, or —O—CO—, where the C1-C4 alkylene group, the C2-C4 alkenylene group, or the $C_2$-$C_4$ alkynylene group is unsubstituted or at least one hydrogen of the C1-C4 alkylene group, the C2-C4 alkenylene group, or the $C_2$-$C_4$ alkynylene group is substituted by halogen, and/or at least one —$CH_2$— of the C1-C4 alkylene group, the C2-C4 alkenylene group, or the $C_2$-$C_4$ alkynylene group is replaced by —O— or —S—, provided that the —O— and —S— do not directly bond to each other;
- X represents hydrogen, halogen, CN, $CF_3$, or $CCl_3$; and
- each of q and r independently represents 0, 1, or 2, and q+r≤1.

In another aspect, the disclosure also provides a liquid-crystal composition. The liquid-crystal composition includes a first component including at least one liquid-crystal compound represented by the above Formula (I). The liquid-crystal composition also includes a third component including at least one liquid-crystal compound represented by Formula (III):

wherein
- R6 represents halogen, —$CF_3$, —OCH=$CF_2$, or —$OCF_3$;
- R5 represents hydrogen, a $C_1$-$C_{10}$ alkyl group, or a $C_2$-$C_{10}$ alkenyl group, where the $C_1$-$C_{10}$ alkyl group or the $C_2$-$C_{10}$ alkenyl group is unsubstituted or at least one —$CH_2$— of the $C_1$-$C_{10}$ alkyl group or the $C_2$-$C_{10}$ alkenyl group is replaced by —O—, —S—, —CO—, —O—CO—, —CO—O—, or —O—CO—O—, and wherein the —O—, —S—, —CO—, —O—CO—, —CO—O—, and —O—CO—O— do not directly bond to one another, and/or at least one hydrogen of the $C_1$-$C_{10}$ alkyl group or the $C_2$-$C_{10}$ alkenyl group is substituted by halogen, CN, or $CF_3$;
- each of A7, A8, A9, and A10 independently represents a 1,4-phenylene group, a 1,4-cyclohexylene group, a divalent dioxabicyclo[2.2.2]octylene group, a divalent trioxabicyclo[2.2.2]octylene group, or a divalent 2,5-indanylene group, where the 1,4-phenylene group, the 1,4-cyclohexylene group, or the divalent 2,5-indanylene group is unsubstituted or at least one hydrogen of the 1,4-phenylene group, the 1,4-cyclohexylene group, or the divalent 2,5-indanylene group is substituted by halogen or CN, and/or at least one —$CH_2$— of the 1,4-cyclohexylene group is replaced by —O—, —NH—, or —S—, provided that the —O—, —NH—, and —S— do not directly bond to one another, or at least one —$CH_2$— of the divalent 2,5-indanylene group is replaced by —O—, —NH—, or —S—, provided that the —O—, —NH—, and —S— do not directly bond to one another;
- each of Z7, Z8 and Z9 independently represents a single bond, a C1-C4 alkylene group, a C2-C4 alkenylene group, a $C_2$-$C_4$ alkynylene group, —CO—O—, or —O—CO—, where the C1-C4 alkylene group, the C2-C4 alkenylene group, or the $C_2$-$C_4$ alkynylene group is unsubstituted or at least one hydrogen of the C1-C4 alkylene group, the C2-C4 alkenylene group, or the $C_2$-$C_4$ alkynylene group is substituted by halogen, and/or at least one —$CH_2$— of the C1-C4 alkylene group, the C2-C4 alkenylene group, or the $C_2$-$C_4$ alkynylene group is replaced by —O— or —S—, and —O— does not directly bond to —O— or —S—, and —S— does not directly bond to —S—, and wherein at least one of Z7, Z8 and Z9 represents —$OCF_2$— or —$CF_2O$—; and
- each of s, t, u, and v independently represents 0, 1, 2, or 3, and s+t+u+v≥3.

A detailed description is given in the following embodiments with reference to the accompanying drawings.

DETAILED DESCRIPTION

In accordance with one aspect of the disclosure, a liquid crystal compound is provided. The liquid crystal compound is represented by Formula (I):

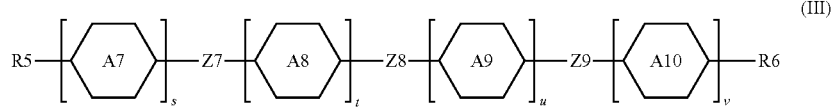

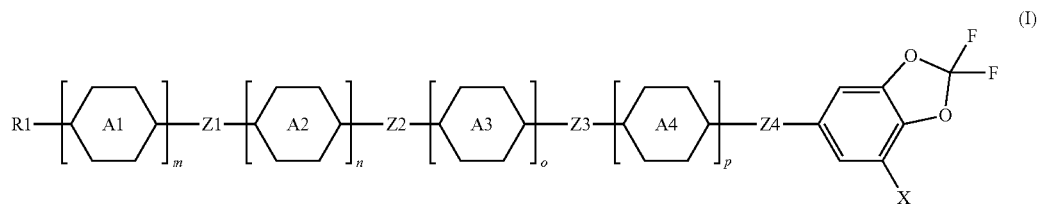

wherein
R1 represents hydrogen, a $C_1$-$C_{10}$ alkyl group, or a $C_2$-$C_{10}$ alkenyl group, where the $C_1$-$C_{10}$ alkyl group or the $C_2$-$C_{10}$ alkenyl group is unsubstituted or at least one —$CH_2$— of the $C_1$-$C_{10}$ alkyl group or the $C_2$-$C_{10}$ alkenyl group is replaced by —O—, —S—, —O—CO—, —OC—O—, or —O—CO—O—, provided that the —O—, —S—, —O—CO—, —OC—O—, and —O—CO—O— do not directly bond to one another, and/or at least one hydrogen of the $C_1$-$C_{10}$ alkyl group or the $C_2$-$C_{10}$ alkenyl group is substituted by halogen, CN, or $CF_3$; each of A1, A2, A3, and A4 independently represents a 1,4-phenylene group, a 1,4-cyclohexylene group, a divalent dioxabicyclo[2.2.2]octylene group, a divalent trioxabicyclo[2.2.2]octylene group, or a divalent 2,5-indanylene group, where the 1,4-phenylene group, the 1,4-cyclohexylene group, or the divalent 2,5-indanylene group is unsubstituted or at least one hydrogen of the 1,4-phenylene group, the 1,4-cyclohexylene group, or the divalent 2,5-indanylene group is substituted by halogen, CN, or $CF_3$, and/or at least one —$CH_2$— of the 1,4-cyclohexylene group is replaced by —O—, —S—, —O—CO—, —OC—O—, or —O—CO—O—, provided that the —O—, —S—, —O—CO—, —OC—O—, and —O—CO—O— do not directly bond to one another, and/or at least one —$CH_2$— of the divalent 2,5-indanylene group is replaced by —O— or —S—, provided that the —O— and —S— do not directly bond to one another;

each of Z1, Z2, Z3, and Z4 independently represents a single bond, a C1-C4 alkylene group, a C2-C4 alkenylene group, a $C_2$-$C_4$ alkynylene group, —O—CO—, or —CO—O—, where the C1-C4 alkylene group, the C2-C4 alkenylene group, or the $C_2$-$C_4$ alkynylene group is unsubstituted or at least one hydrogen of the C1-C4 alkylene group, the C2-C4 alkenylene group, or the $C_2$-$C_4$ alkynylene group is substituted by halogen, and/or at least one —$CH_2$— of the C1-C4 alkylene group, the C2-C4 alkenylene group, or the $C_2$-$C_4$ alkynylene group is replaced by —O— or —S—, provided that the —O— and —S-do not directly bond to each other;

X represents hydrogen, halogen, CN, $CF_3$, or $CCl_3$; and
each of m, n, o, and p independently represents 0 or 1, and m+n+o+p>0.

In this disclosure, when Zn (e.g., Z1, Z2, Z3, etc.) represents a single bond, the two opposite groups of the Zn are directly bonded to each other. For example, when Z1 represents a single bond, groups A1 and A2 are directly bonded to each other.

In accordance with some embodiments, in Formula (I), R1 represents hydrogen, a $C_1$-$C_{10}$ alkyl group, or a $C_2$-$C_{10}$ alkenyl group. In some embodiments, R1 may be, for example, a methyl group, an ethyl group, a propyl group, an isopropyl group, an n-butyl group, a sec-butyl group, an isobutyl group, a tertiary butyl group, a pentyl group, a hexyl group, a heptyl group, an octyl group, a nonyl group, a decyl group, a fluoromethyl group, a fluoroethyl group, a fluoropropyl group, a fluorobutyl group, a fluoropentyl group, a fluorohexyl group, a fluoroheptyl group, a fluorooctyl group, a fluorononyl group, a fluorodecyl group, a methoxy group, an ethoxy group, a propoxy group, an isopropoxy group, an n-butoxy group, a sec-butoxy group, an isobutoxy group, a tert-butoxy group, a pentyloxy group, a hexyloxy group, a heptyloxy group, a octyloxy group, a nonyloxy group, a decyloxy group, a fluoromethoxy group, a fluoroethoxy group, a methoxymethyl group, a methoxyethyl group, a methylsulfanyl group, a vinyl group or a propenyl group. Furthermore, R1 may be unsubstituted or at least one —$CH_2$— of the $C_1$-$C_{10}$ alkyl group or the $C_2$-$C_{10}$ alkenyl group is replaced by —O—, —S—, —O—CO—, —OC—O—, or —O—CO—O—, provided that the —O—, —S—, —O—CO—, —OC—O—, and —O—CO—O— do not directly bond to one another, and/or at least one hydrogen of the $C_1$-$C_{10}$ alkyl group or the $C_2$-$C_{10}$ alkenyl group is substituted by halogen, CN, or $CF_3$.

In accordance with some embodiments, in Formula (I), each of A1, A2, A3, and A4 independently represents a 1,4-phenylene group, a 1,4-cyclohexylene group, a divalent dioxabicyclo[2.2.2.2]octylene group, a divalent trioxabicyclo[2.2.2]octylene group, or a divalent 2,5-indanylene group. The 1,4-phenylene group, the 1,4-cyclohexylene group, or the divalent 2,5-indanylene group may be unsubstituted or at least one hydrogen of the 1,4-phenylene group, the 1,4-cyclohexylene group, or the divalent 2,5-indanylene group is substituted by halogen, CN, or $CF_3$, and/or at least one —$CH_2$— of the 1,4-cyclohexylene group is replaced by —O—, —S—, —O—CO—, —OC—O—, or —O—CO—O—, provided that the —O—, —S—, —O—CO—, —OC—O—, and —O—CO—O— do not directly bond to one another, and/or at least one —$CH_2$— of the divalent 2,5-indanylene group is replaced by —O— or —S—, provided that the —O— and —S— do not directly bond to one another. In some embodiments, each of A1, A2, A3, and A4 may independently be, for example,

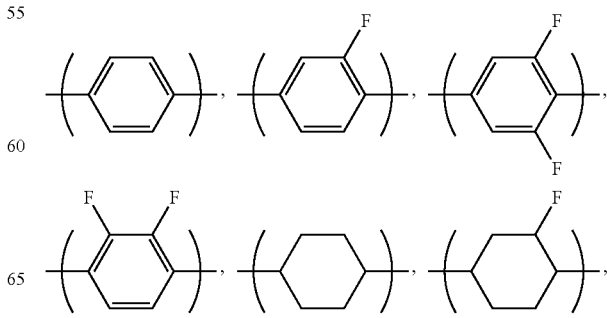

-continued

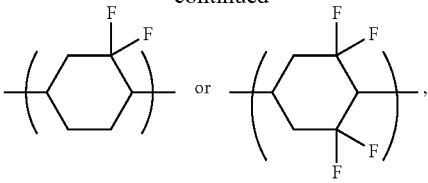

and m+n+o+p>0, in accordance with some embodiments. In addition, at least one of A1, A2, and A3 is a 1,4-phenylene group or a 1,4-cyclohexylene group, and at least one hydrogen of the 1,4-phenylene group or the 1,4-cyclohexylene group is substituted by halogen, CN, or $CF_3$, in accordance with some embodiments. In such embodiments, at least one of m, n, o, and p may be 0.

In accordance with some embodiments, in Formula (I), each of Z1, Z2, Z3, and Z4 independently represents a single bond, a C1-C4 alkylene group, a C2-C4 alkenylene group, a $C_2$-$C_4$ alkynylene group, —O—CO—, or —CO—O—. The C1-C4 alkylene group, the C2-C4 alkenylene group, or the $C_2$-$C_4$ alkynylene group may be unsubstituted or at least one hydrogen of the C1-C4 alkylene group, the C2-C4 alkenylene group, or the $C_2$-$C_4$ alkynylene group is substituted by halogen, and/or at least one —$CH_2$— of the C1-C4 alkylene group, the C2-C4 alkenylene group, or the $C_2$-$C_4$ alkynylene group is replaced by —O— or —S—, provided that the —O— and —S— do not directly bond to each other. In some embodiments, at least one of Z1, Z2, Z3, and Z4 is —$CF_2$O— or —$OCF_2$—.

Furthermore, in order to provide the liquid crystal compound with high dielectric anisotropy (Δε), good light stability and thermal stability, proper rotational viscosity coefficient (γ1), lower ratio of rotational viscosity coefficient to dielectric anisotropy (i.e., γ1/Δε), and high refractive anisotropy (Δn), at least one of Z3 and Z4 is —$CF_2$O— or —$OCF_2$—, in accordance with some embodiments.

In accordance with some embodiments, in Formula (I), X represents hydrogen, halogen, CN, $CF_3$, or $CCl_3$. In order to provide the liquid crystal compound with high dielectric anisotropy (Δε), good light stability and thermal stability, proper rotational viscosity coefficient (γ1), and lower ratio of rotational viscosity coefficient to dielectric anisotropy (i.e., γ1/Δε), X is H or F, in accordance with some embodiments.

Furthermore, in order to provide the liquid crystal compound with high dielectric anisotropy (Δε), good light stability and thermal stability, suitable rotational viscosity coefficient (γ1), and high refractive anisotropy (Δn), at least one of A1, A2, and A3 is

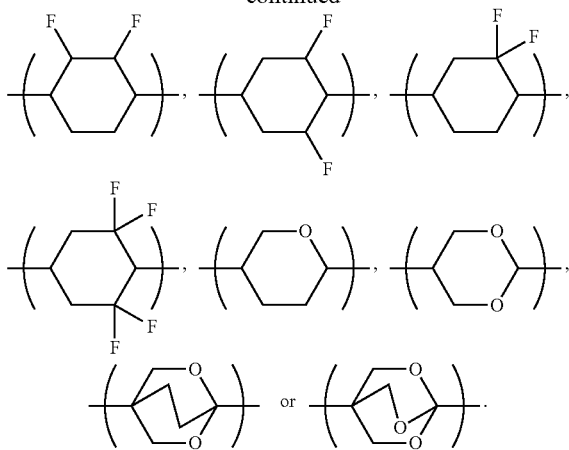

In accordance with some embodiments, the liquid crystal compound is represented by Formula (I-A), (I-B), or (I-C):

Formula (I-A)

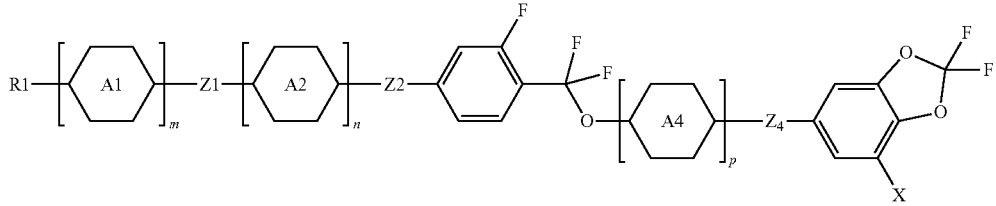

Formula (I-B)

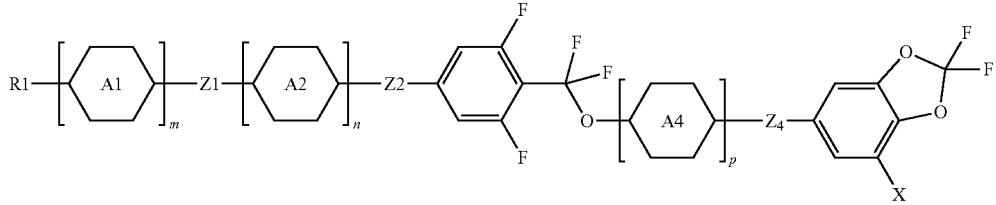

-continued

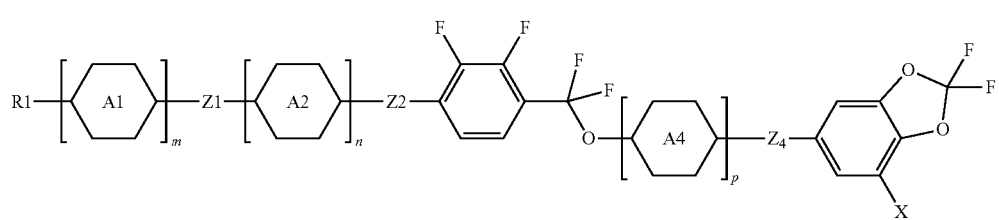

Formula (I-C)

wherein
R1 represents hydrogen, a $C_1$-$C_{10}$ alkyl group, or a $C_2$-$C_{10}$ alkenyl group, where the $C_1$-$C_{10}$ alkyl group or the $C_2$-$C_{10}$ alkenyl group is unsubstituted or at least one —$CH_2$— of the $C_1$-$C_{10}$ alkyl group or the $C_2$-$C_{10}$ alkenyl group is replaced by —O—, —S—, —OCO—, —OC—O—, or —O—CO—O—, provided that the —O—, —S—, —O—CO—, —OC—O—, and —O—CO—O— do not directly bond to one another, and/or at least one hydrogen of the $C_1$-$C_{10}$ alkyl group or the $C_2$-$C_{10}$ alkenyl group is substituted by halogen, CN, or $CF_3$;

each of A1, A2, and A4 independently represents a 1,4-phenylene group, a 1,4-cyclohexylene group, a divalent dioxabicyclo[2.2.2]octylene group, a divalent trioxabicyclo[2.2.2]octylene group, or a divalent 2,5-indanylene group, where the 1,4-phenylene group, the 1,4-cyclohexylene group, or the divalent 2,5-indanylene group is unsubstituted or at least one hydrogen of the 1,4-phenylene group, the 1,4-cyclohexylene group, or the divalent 2,5-indanylene group is substituted by halogen, CN, or $CF_3$, and/or at least one —$CH_2$— of the 1,4-cyclohexylene group is replaced by —O—, —S—, —O—CO—, —OC—O—, or —O—CO—O—, provided that the —O—, —S—, —O—CO—, —OC—O—, and —O—CO—O— do not directly bond to one another, and/or at least one —$CH_2$— of the divalent 2,5-indanylene group is replaced by —O— or —S—, provided that the —O— and —S— do not directly bond to one another;

each of Z1, Z2, and Z4 independently represents a single bond, a C1-C4 alkylene group, a C2-C4 alkenylene group, a $C_2$-$C_4$ alkynylene group, —$CF_2O$—, —$OCF_2$—, —O—CO—, or —CO—O—, where the C1-C4 alkylene group, the C2-C4 alkenylene group, or the $C_2$-$C_4$ alkynylene group is unsubstituted or at least one hydrogen of the C1-C4 alkylene group, the C2-C4 alkenylene group, or the $C_2$-$C_4$ alkynylene group is substituted by halogen, and/or at least one —$CH_2$— of the C1-C4 alkylene group, the C2-C4 alkenylene group, or the $C_2$-$C_4$ alkynylene group is replaced by —O— or —S—, provided that the —O— and —S— do not directly bond to each other;

X represents hydrogen, halogen, CN, $CF_3$, or $CCl_3$; and
each of m, n, and p independently represents 0 or 1, and m+n+p>0.

Furthermore, in accordance with some embodiments, the liquid crystal compound is represented by Formula (I-D), (I-E), (I-F), (I-G), or (I-H):

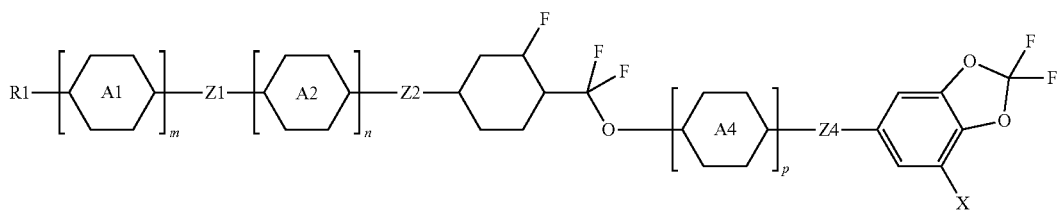

Formula (I-D)

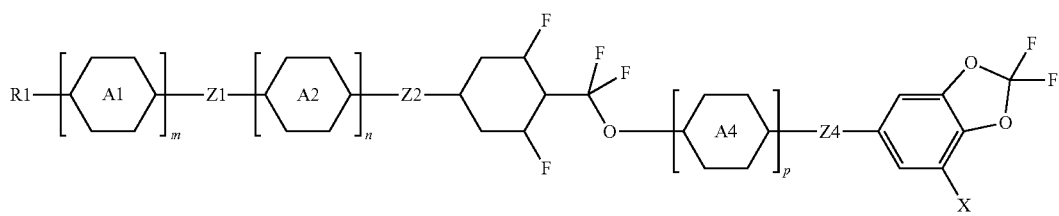

Formula (I-E)

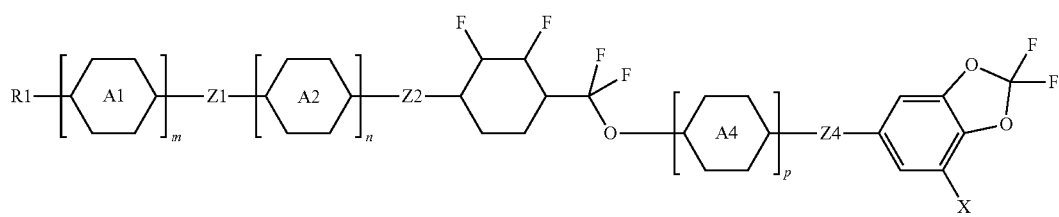

Formula (I-F)

-continued

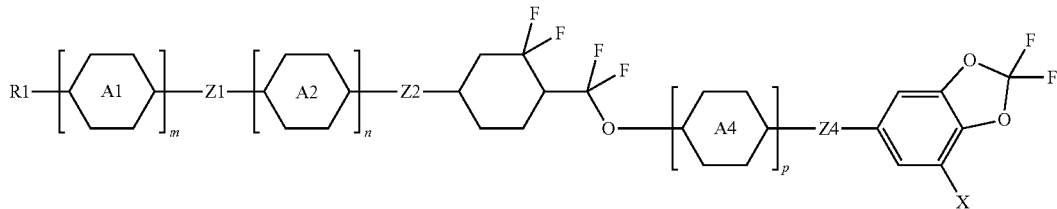

Formula (I-G)

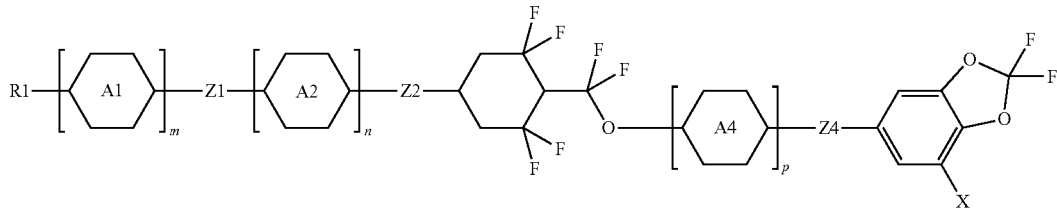

Formula (I-H)

wherein
R1 represents hydrogen, a $C_1$-$C_{10}$ alkyl group, or a $C_2$-$C_{10}$ alkenyl group, where the $C_1$-$C_{10}$ alkyl group or the $C_2$-$C_{10}$ alkenyl group is unsubstituted or at least one —$CH_2$— of the $C_1$-$C_{10}$ alkyl group or the $C_2$-$C_{10}$ alkenyl group is replaced by —O—, —S—, —O—CO—, —OC—O—, or —O—CO—O—, provided that the —O—, —S—, —O—CO—, —OC—O—, and —O—CO—O— do not directly bond to one another, and/or at least one hydrogen of the $C_1$-$C_{10}$ alkyl group or the $C_2$-$C_{10}$ alkenyl group is substituted by halogen, CN, or $CF_3$;

each of A1, A2, and A4 independently represents a 1,4-phenylene group, a 1,4-cyclohexylene group, a divalent dioxabicyclo[2.2.2]octylene group, a divalent trioxabicyclo[2.2.2]octylene group, or a divalent 2,5-indanylene group, where the 1,4-phenylene group, the 1,4-cyclohexylene group, or the divalent 2,5-indanylene group is unsubstituted or at least one hydrogen of the 1,4-phenylene group, the 1,4-cyclohexylene group, or the divalent 2,5-indanylene group is substituted by halogen, CN, or $CF_3$, and/or at least one —$CH_2$— of the 1,4-cyclohexylene group is replaced by —O—, —S—, —O—CO—, —OC—O—, or —O—CO—O—, provided that the —O—, —S—, —O—CO—, —OC—O—, and —O—CO—O— do not directly bond to one another, and/or at least one —$CH_2$— of the divalent 2,5-indanylene group is replaced by —O— or —S—, provided that the —O— and —S— do not directly bond to one another;

each of Z1, Z2, and Z4 independently represents a single bond, a C1-C4 alkylene group, a C2-C4 alkenylene group, a $C_2$-$C_4$ alkynylene group, —$CF_2O$—, —$OCF_2$—, —O—CO—, or —CO—O—, where the C1-C4 alkylene group, the C2-C4 alkenylene group, or the $C_2$-$C_4$ alkynylene group is unsubstituted or at least one hydrogen of the C1-C4 alkylene group, the C2-C4 alkenylene group, or the $C_2$-$C_4$ alkynylene group is substituted by halogen, and/or at least one —$CH_2$— of the C1-C4 alkylene group, the C2-C4 alkenylene group, or the $C_2$-$C_4$ alkynylene group is replaced by —O— or —S—, provided that the —O— and —S— do not directly bond to each other;

X represents hydrogen, halogen, CN, $CF_3$, or $CCl_3$; and
each of m, n, and p independently represents 0 or 1, and m+n+p>.

For clarity of discussion, the liquid crystal compounds used in this disclosure are represented by the combinations of the code names. For example, the oxygen atom is represented by the code name O, and the fluorine atom is represented by the code name F. The structure units and their corresponding code name are list in Table 1.

TABLE 1

| Code | Structure |
|---|---|
| P | X—⬡—Y |
| G | X—⬡(F)—Y |
| U | X—⬡(F,F)—Y |
| UF | (X—⬡(F,F,F)—F) |
| Y | X—⬡(F,F)—Y |

TABLE 1-continued

| Symbol | Structure |
|---|---|
| X | 2,5-difluoro-1,4-phenylene (X and Y on benzene ring with F at 2,5 positions) |
| C | trans-1,4-cyclohexylene |
| Cp | 1,3-cyclopentylene |
| 2F | –C(X)=CF$_2$ (1,2-difluorovinylene with F,F on one carbon) |
| O2F | X–O–CH=CF$_2$ |
| M | 2-methyl-1,4-phenylene |
| E | 2-ethyl-1,4-phenylene |
| V | X–CH=CH–Y (trans vinylene) |
| VI | X–(CH=CH–CH$_3$) |
| I | 2,5-indanylene (X on benzene ring, Y on cyclopentane) |
| RI | 2,5-indanylene (X on cyclopentane, Y on benzene ring) |
| Z | –CF=CF– (X and Y on doubly-bonded carbons, each bearing F) |
| T | X–C≡C–Y |
| K | 1-fluoro-cyclopent-1-en-3-yl (X on C1, F on C2, Y on C3) |
| L | 2-fluoro-cyclohex-1-en-4-yl (X on C1, F on C2, Y on C4) |
| to | 2,6,7-trioxabicyclo[2.2.2]octane-1,4-diyl |
| do | 2,6-dioxabicyclo[2.2.2]octane-1,4-diyl |
| Q | X–CF$_2$–O–Y |
| D | 1,3-dioxane-2,5-diyl |
| Iof | 2,2-difluoro-1,3-benzodioxole-5-yl |
| Ioff | 2,2,4-trifluoro-1,3-benzodioxole-5-yl (parenthesized) |
| C(F) | 2-fluoro-1,4-cyclohexylene (parenthesized) |
| C(FF) | 2,2-difluoro-1,4-cyclohexylene (parenthesized) |
| C(FF)(F) | 2,2,3-trifluoro-1,4-cyclohexylene (parenthesized) |
| C(FF)(FF) | 2,2,3,3-tetrafluoro-1,4-cyclohexylene (parenthesized) |

TABLE 1-continued

| | |
|---|---|
| C(F)(F) | 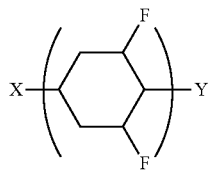 |
| C(F)(F)' | 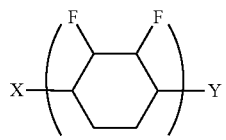 |

It should be noted that, in the structure units of Table 1, X represents the bonding position of the left-end bonding group of the structure unit, and Y represents the bonding position of the right-end bonding group of the structure unit. In other words, if the structure unit only has X, this structure unit is the rightmost structure unit of the liquid crystal compound. Furthermore, a normal-sized number represents an alkyl group with carbon atoms equal to this number. For example, the code name 3CCV represents the compound having a $C_3$ alkyl group, the structure unit C, the structure unit C, and the structure unit V, from the leftmost end to the rightmost end sequentially. In other words, the code name 3CCV represents the following compound:

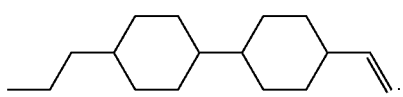 [SMILES: C=CC1CCC(C2CCC(CCC)CC2)CC1]

In addition, the code names are combined according to the position and direction as shown in Table 1. For example, the code name 3PGQIof represents the following compound:

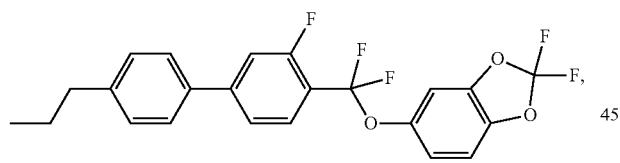

rather than

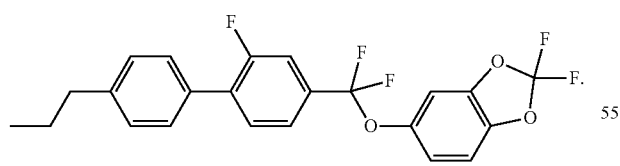

In accordance with some embodiments, the liquid crystal compound represented by Formula (I) may be, for example, 3CPIof, 3PPIof, 2toUQIof, 3toUQIof, 3doUQIof, 3RIUQIof, 3PQUQIof, 3GGIof, 3GUIof, 3PUQIof, 3PYQIof, 3CGQIof, 3CUQIof, 3CYQIof, 3PC(F)QIof, 3PC(F)(F)'QIof, 3PC(F)(F)QIof, 3PC(FF)QIof, 3PC(FF)(FF)QIof, 3CC(F)QIof, 3CC(F)(F)'QIof, 3CC(F)(F)QIof, 2PGQIof, 2PYQIof, 2PC(FF)(FF)QIof, 2CC(F)QIof, 5CC(F)(F')QIof, 5PYQIof, 3CPIoff, 3PPIoff, 2toUQIoff, 3toUQIoff, 3doUQIof, 3RIUQIoff, 3PQUQIoff, 3GGIoff, 3GUIoff, 3PUQIoff, 3PYQIoff, 3CGQIoff, 3CUQIoff, 3CYQIoff, 3PC(F)QIoff, 3PC(F)(F)'QIoff, 3PC(F)(F)QIoff, 3PC(FF)QIoff, 3PC(FF)(FF)QIoff, 3CC(F)QIoff, 3CC(F)(F)'QIoff, 3CC(F)(F)QIoff, 2PGQIoff, 2PYQIoff, 2PC(FF)(FF)QIoff, 2CC(F)QIoff, 5CC(F)(F')QIof, or 5PYQIoff. In accordance with some embodiments, the structure unit Q (—$CF_2O$—) may be replaced by —$OCF_2$— or $OCF_2O$.

Because the liquid crystal compounds have the structure represented by Formula (I), the liquid crystal compounds in the disclosure have high dielectric anisotropy ($\Delta\varepsilon>8$), good light stability and thermal stability, proper rotational viscosity coefficient ($\gamma1<150$), lower ratio of rotational viscosity coefficient to dielectric anisotropy ($\gamma1/\Delta\varepsilon<5$), and higher refractive anisotropy ($\Delta n>0.1$). Therefore, the display using the liquid crystal composition including the liquid crystal compounds of the disclosure may have better display performance, lower driving voltage, and faster response speed.

In accordance with another aspect of the disclosure, a liquid crystal composition is also provided. The liquid crystal composition includes a first component, which contains one or more liquid crystal compounds represented by Formula (I). In some embodiments, the liquid crystal composition may include a second component, which contains one or more liquid crystal compounds represented by Formula (II):

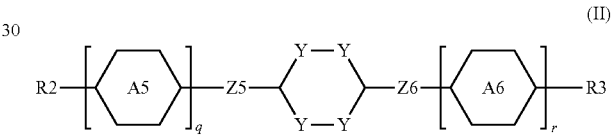

wherein

R3 represents a $C_1$-$C_{10}$ alkyl group, a $C_2$-$C_{10}$ alkenyl group, halogen, —$CF_3$, —$OCH=CF_2$, or —$OCF_3$;

R2 represents hydrogen, a $C_1$-$C_{10}$ alkyl group, or a $C_2$-$C_{10}$ alkenyl group, where the $C_1$-$C_{10}$ alkyl group or the $C_2$-$C_{10}$ alkenyl group is unsubstituted or at least one —$CH_2$— of the $C_1$-$C_{10}$ alkyl group or the $C_2$-$C_{10}$ alkenyl group is replaced by —O—, —S—, —CO—, —O—CO—, —CO—O—, or —O—CO—O—, and wherein the —O—, —S—, —CO—, —O—CO—, —CO—O—, and —O—CO—O— do not directly bond to one another, and/or at least one hydrogen of the $C_1$-$C_{10}$ alkyl group or the $C_2$-$C_{10}$ alkenyl group is substituted by halogen, CN, or $CF_3$;

Y represents —$C(R4)_2$-, —O—, or —S—, and —O— does not directly bond to —O— or —S—, and —S— does not directly bond to —S—, where each of R4 independently represents hydrogen or halogen;

each of A5 and A6 independently represents a 1,4-phenylene group, a 1,4-cyclohexylene group, a divalent dioxabicyclo[2.2.2]octylene group, a divalent trioxabicyclo[2.2.2]octylene group, or a divalent 2,5-indanylene group, where the 1,4-phenylene group, the 1,4-cyclohexylene group, or the divalent 2,5-indanylene group is unsubstituted or at least one hydrogen of the 1,4-phenylene group, the 1,4-cyclohexylene group, or the divalent 2,5-indanylene group is substituted by halogen or CN, and/or at least one —$CH_2$— of the 1,4-cyclohexylene group is replaced by —O—, —NH—, or —S—, provided that the —O—, —NH—, and —S— do not directly bond to one another, or at least one —$CH_2$— of the divalent 2,5-indanylene group is replaced by —O—, —NH—, or —S—, provided that the —O—, —NH—, and —S— do not directly bond to one another;

each of Z5 and Z6 independently represents a single bond, a C1-C4 alkylene group, a C2-C4 alkenylene group, a $C_2$-$C_4$ alkynylene group, —CO—O—, or —O—CO—, where the C1-C4 alkylene group, the C2-C4 alkenylene group, or the $C_2$-$C_4$ alkynylene group is unsubstituted or at least one hydrogen of the C1-C4 alkylene group, the C2-C4 alkenylene group, or the $C_2$-$C_4$ alkynylene group is substituted by halogen, and/or at least one —$CH_2$— of the C1-C4 alkylene group, the C2-C4 alkenylene group, or the $C_2$-$C_4$ alkynylene group is replaced by —O— or —S—, provided that the —O— and —S— do not directly bond to each other;

X represents hydrogen, halogen, CN, $CF_3$, or $CCl_3$; and each of q and r independently represents 0, 1, or 2, and q+r≥1.

In some embodiments, the liquid crystal compound represented by Formula (II) may be, for example, 2CCGF, 3CCGF, 5CCGF, 3CCV, 3CCP1, 3CPTP2, 3CPP2, 2CPGF, 3CPGF, 2CPPF, or 3CPPF. For the purpose of simplicity and clarity, these liquid crystal compounds are represented by the code name, and relationship between the code name and the corresponding structure is shown in Table 1.

In some embodiments, the liquid crystal compound represented by Formula (I) is 0.1-50 wt %, and the liquid crystal compound represented by Formula (II) is 10-99 wt %, based on a total weight of the liquid crystal composition. In other embodiments, the liquid crystal compound represented by Formula (I) is 0.1-50 wt %, and the liquid crystal compound represented by Formula (II) is 10-99.9 wt %, based on a total weight of the liquid crystal composition. In other embodiments, the liquid crystal compound represented by Formula (I) is 3-30 wt %, and the liquid crystal compound represented by Formula (II) is 15-97 wt %, based on a total weight of the liquid crystal composition.

In accordance with another aspect of the disclosure, a liquid crystal composition is also provided. The liquid crystal composition includes a first component, which contains one or more liquid crystal compounds represented by the above Formula (I). In some embodiments, the liquid crystal composition also includes a third component, which contains one or more liquid crystal compounds represented by Formula (III):

each of A7, A8, A9, and A10 independently represents a 1,4-phenylene group, a 1,4-cyclohexylene group, a divalent dioxabicyclo[2.2.2]octylene group, a divalent trioxabicyclo[2.2.2]octylene group, or a divalent 2,5-indanylene group, where the 1,4-phenylene group, the 1,4-cyclohexylene group, or the divalent 2,5-indanylene group is unsubstituted or at least one hydrogen of the 1,4-phenylene group, the 1,4-cyclohexylene group, or the divalent 2,5-indanylene group is substituted by halogen or CN, and/or at least one —$CH_2$— of the 1,4-cyclohexylene group is replaced by —O—, —NH—, or —S—, provided that the —O—, —NH—, and —S— do not directly bond to one another, or at least one —$CH_2$— of the divalent 2,5-indanylene group is replaced by —O—, —NH—, or —S—, provided that the —O—, —NH—, and —S— do not directly bond to one another;

each of Z7, Z8 and Z9 independently represents a single bond, a C1-C4 alkylene group, a C2-C4 alkenylene group, a $C_2$-$C_4$ alkynylene group, —CO—O—, or —O—CO—, where the C1-C4 alkylene group, the C2-C4 alkenylene group, or the $C_2$-$C_4$ alkynylene group is unsubstituted or at least one hydrogen of the C1-C4 alkylene group, the C2-C4 alkenylene group, or the $C_2$-$C_4$ alkynylene group is substituted by halogen, and/or at least one —$CH_2$— of the C1-C4 alkylene group, the C2-C4 alkenylene group, or the $C_2$-$C_4$ alkynylene group is replaced by —O— or —S—, and —O— does not directly bond to —O— or —S—, and —S— does not directly bond to —S—, and wherein at least one of Z7, Z8 and Z9 represents —$OCF_2$— or —$CF_2O$—; and each of s, t, u, and v independently represents 0, 1, 2, or 3, and s+t+u+v≥3.

In accordance with some embodiments, the first component may be, for example, 3CPIof, 3PPIof, 3PUQIof, 3PYQIof, 3CGQIof, 3CUQIof, 3CYQIof, 2PGQIof, 2PYQIof, 5PYQIof, 2toUQIof, 3toUQIof, 3doUQIof, 3RIUQIof, 3PQUQIof, 3GGIof, 3GUIof, 3CPIoff, 3PPIoff, 3PUQIoff, 3PYQIoff, 3CGQIoff, 3CUQIoff, 3CYQIoff, 2PGQIoff, or 2PYQIof, 5PYQIoff, 2toUQIoff, 3toUQIoff, 3toUQIoff, 3RIUQIoff, 3PQUQIoff, 3GGIoff, 3GUIoff. In some embodiments, the structure unit —$CF_2O$— (i.e., the code name Q) may be replaced by —$OCF_2$— or —$OCF_2O$—.

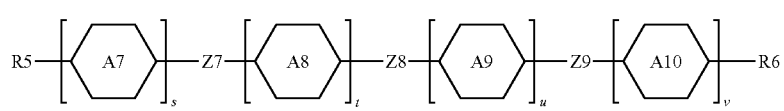

(III)

wherein

R6 represents halogen, —$CF_3$, —OCH=$CF_2$, or —$OCF_3$;

R5 represents hydrogen, a $C_1$-$C_{10}$ alkyl group, or a $C_2$-$C_{10}$ alkenyl group, where the $C_1$-$C_{10}$ alkyl group or the $C_2$-$C_{10}$ alkenyl group is unsubstituted or at least one —$CH_2$— of the $C_1$-$C_{10}$ alkyl group or the $C_2$-$C_{10}$ alkenyl group is replaced by —O—, —S—, —CO—, —O—CO—, —CO—O—, or —O—CO—O—, and wherein the —O—, —S—, —CO—, —O—CO—, —CO—O—, and —O—CO—O— do not directly bond to one another, and/or at least one hydrogen of the $C_1$-$C_{10}$ alkyl group or the $C_2$-$C_{10}$ alkenyl group is substituted by halogen, CN, or $CF_3$;

In these embodiments, each of the liquid crystal compounds represented by Formula (I) has structure unit Iof or Ioff (the structure is shown in Table 1). The structure unit Iof or Ioff may provide the liquid crystal compounds with high dielectric anisotropy (Δε), low rotational viscosity coefficient (γ1), high elastic coefficient (K11), and good light stability and thermal stability. Therefore, the liquid crystal composition in these embodiments may have lower ratio of rotational viscosity coefficient to elastic coefficient (i.e., γ1/K11), and the response speed of the liquid crystal molecule are increased when the voltage is applied. Furthermore, the display using the liquid crystal composition in the disclosure may have better display performance, lower driving voltage, and lower energy consumption.

In addition, when Z4 is —CF$_2$O— or —OCF$_2$—, the liquid crystal compound represented by Formula (I) has the structure unit —CF$_2$O-Iof or —OCF$_2$—Iof. These structure units may also increase the elastic coefficient (K11) and reduce the ratio of rotational viscosity coefficient to elastic coefficient (i.e., γ1/K11). Therefore, the response speed of the liquid crystal composition is improved. It is advantageous to switch the bright state and the dark state and improve the afterimage issue.

In some embodiments, the first component only includes one liquid crystal compound represented by Formula (I), and Z4 of this liquid crystal compound is not —CF$_2$— or —OCF$_2$—. In some embodiments, the first component includes at least two liquid crystal compounds represented by Formula (I), and Z4 of at least one of these liquid crystal compounds is not —CF$_2$O— or —OCF$_2$—. In other embodiments, the first component includes at least two liquid crystal compounds represented by Formula (I), and Z1, Z2, Z3, and Z4 of at least one of these liquid crystal compounds are not —CF$_2$O— or —OCF$_2$—. In some embodiments, the first component includes at least two liquid crystal compounds represented by Formula (I). Z4 of at least one of these liquid crystal compounds is not —CF$_2$O— or —OCF$_2$—, and Z4 of other one of the at least one of these liquid crystal compounds is —CF$_2$O— or —OCF$_2$—.

In accordance with some embodiments, the liquid crystal composition also includes a third component, which contains one or more liquid crystal compounds represented by Formula (III). The third component may be, for example, 2toUQU-O$_2$F, 3toUQU-O$_2$F, 5toUQU-O$_2$F, 2doUQUF, 3doUQUF, 5doUQUF, 2doPUO$_2$F, 3doPUO$_2$F, 5doPUO$_2$F, RIGUQUF, 1RIGUQUF, 2RIGUQUF, 3RIGUQUF, 5RIGUQUF, 2PUQUF, 3PUQUF, 5PUQUF, 2RIUQUF, 3RIUQUF, 5RIUQUF, 2RIGUQU-O$_2$F, 3RIGUQU-O$_2$F, 5RIGUQU-$_2$F, 2RIUQUOCF$_3$, 3RIUQUOCF$_3$, 5RIUQUOCF$_3$, 2CUQUF, 3CUQUF, or 5CUQUF.

For the liquid crystal compounds represented by Formula (III), when one of Z7, Z8, and Z9 is —CF$_2$O— or —OCF$_2$—, the rotational viscosity coefficient (γ1) will be reduced, and the dielectric anisotropy (Δε) will be increased. Therefore, if the third component includes the liquid crystal compound having the structure unit —CF$_2$O— or —OCF$_2$—, the dielectric anisotropy and the rotational viscosity coefficient of the liquid crystal composition will be improved further.

For the liquid crystal compounds represented by Formula (II), when one of A7, A8, A9, and A10 is structure unit R1, to, or do (the corresponding structures are shown in Table 1), the dielectric anisotropy (Δε) will be increased. Furthermore, for the liquid crystal compounds represented by Formula (III), when one of A7, A8, A9, and A10 is structure unit P (the corresponding structure is shown in Table 1), the elastic coefficient (K11) will be increased. Therefore, by properly choosing A7, A8, A9, and A10 of the liquid crystal compounds represented by Formula (III), the dielectric anisotropy and the elastic coefficient may be adjusted in a desired range.

In some embodiments, the third component includes one or more liquid crystal compounds represented by Formula (III), and Z7, Z8, or Z9 of at least one of these liquid crystal compounds is —CF$_2$O— or —OCF$_2$—. In some embodiments, the third component includes one or more liquid crystal compounds represented by Formula (III), and Z7, Z8, or Z9 of at least one of these liquid crystal compounds is —CF$_2$O— or —OCF$_2$—, and A7, A8, A9, or A10 of at least one of these liquid crystal compounds is RI, to, do, or P.

In accordance with some embodiments, the liquid crystal composition also includes a fourth component, which contains one or more liquid crystal compounds represented by Formula (IV):

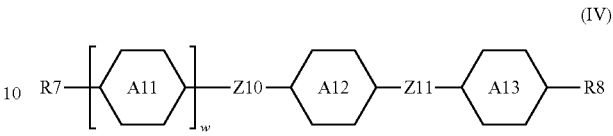

wherein
each of R7 and R8 represents a C$_1$-C$_{15}$ alkyl group or a C$_2$-C$_{15}$ alkenyl group, wherein at least one —CH$_2$— of the C$_1$-C$_{15}$ alkyl group or the C$_2$-C$_{15}$ alkenyl group is replaced by —O—, and wherein —O— does not directly bond to —O—;
each of A11, A12, and A13 independently represents a 1,4-phenylene group, a 1,4-cyclohexylene group, or a 2,5-tetrahydropyranyl group, wherein the 1,4-phenylene group, the 1,4-cyclohexylene group, or the 2,5-tetrahydropyranyl group is unsubstituted or at least one hydrogen of the 1,4-phenylene group, the 1,4-cyclohexylene group, or the 2,5-tetrahydropyranyl group is substituted by fluorine;
each of Z10 and Z11 independently represents a single bond, a C1-C4 alkylene group, a C2-C4 alkenylene group, a C$_2$-C$_4$ alkynylene group, —CO—O—, or —O—CO—, wherein the C1-C4 alkylene group, the C2-C4 alkenylene group, or the C$_2$-C$_4$ alkynylene group is unsubstituted or at least one hydrogen of the C1-C4 alkylene group, the C2-C4 alkenylene group, or the C$_2$-C$_4$ alkynylene group is substituted by halogen or CN, and/or at least one —CH$_2$— of the C1-C4 alkylene group, the C2-C4 alkenylene group, or the C$_2$-C$_4$ alkynylene group is replaced by —O— or —S—, and —O— does not directly bond to —O— or —S—, and —S— does not directly bond to —S—; and
w represents an integer greater than or equal to 0.

The fourth component may be, for example, 3CCV, 3CC4, 3CC5, 3CCV1, 5PP1, 1PP2V1, 1PTPO2, 3PtPO1, 3CPTP2, 3CPTP4, V2PTP2V, 3PTP2V, 2CPGF, 3CPGF, 3CCGOCF$_3$, 3CCPOCF$_3$, 2CPPF, 3CPPF, 2CCPUF, 3CCGUF, 3PGUF, or 3CPUF.

In the liquid crystal compounds represented by Formula (I) or (III), some hydrogen atoms may be substituted by fluorine atoms. Fluorine atom has extremely high electronegativity, extremely small atom volume, high specific resistance, and high conductivity. Therefore, when more hydrogen atoms of a liquid crystal compound are substituted by fluorine atoms, the dielectric constant of the liquid crystal compound will be higher. In the disclosure, the fourth component may be used alone or in combination with other component as mother liquor of the liquid crystal composition. In comparison with the liquid crystal compounds represented by Formula (I) or (III), the liquid crystal compounds represented by Formula (IV) has fewer, or even no hydrogen atoms substituted by fluorine atoms. Therefore, the liquid crystal compounds represented by Formula (IV) has relative lower rotational viscosity coefficient. Accordingly, when the fourth component is used as mother liquor which has a relative high content ratio in the liquid crystal composition, the liquid crystal composition may have lower viscosity.

In the liquid crystal composition of the disclosure, the first component and the third component may have different properties and functions. Therefore, by properly choosing the first component and the third component and adjusting their contents, the dielectric anisotropy and the elastic coefficient of the liquid crystal composition may be controlled in a desired range. The liquid crystal composition of the disclosure may have reduced rotational viscosity coefficient ($\gamma 1<60$) or increased elastic coefficient ($K11>9$) to improve the ratio of rotational viscosity coefficient to elastic coefficient ($\gamma 1/K11<5.5$), while maintaining the dielectric anisotropy at a sufficiently high value ($\Delta \varepsilon >5$). In other words, the liquid crystal composition of the disclosure may achieve a high dielectric anisotropy without incurring high viscosity, and may have higher elastic coefficient. In addition, the liquid crystal composition may include an additional fourth component as mother liquor optionally.

In accordance with some embodiments, the first component is 1-45 wt %, the third component is 1-45 wt %, and the fourth component is 10-7 wt %, based on a total weight of the liquid crystal composition. In some embodiments, the first component is 1-20 wt %, for example, 1.5-15 wt %; and the third component is 15-40 wt %, for example, 20-40 wt %, based on a total weight of the liquid crystal composition. In some embodiments, the fourth component is 15-70 wt %, based on a total weight of the liquid crystal composition. In some embodiments, the total content of the first component and the third component is 2-90 wt %, for example, 5-50 wt %, based on a total weight of the liquid crystal composition.

It should be realized that the liquid crystal composition in the disclosure may further include additional additives, such as, chiral agent. UV stabilizer, antioxidant, free radical scavenger, nanoparticles, and so on. Furthermore, in accordance with some embodiments, the liquid crystal composition in the disclosure may further include other applicable liquid crystal compounds.

A detailed description is given with reference to the following examples.

EXAMPLES

Manufacturing methods of the liquid crystal compound represented by Formula (I) are described as follows.

Example 1 Liquid Crystal Compound (a)

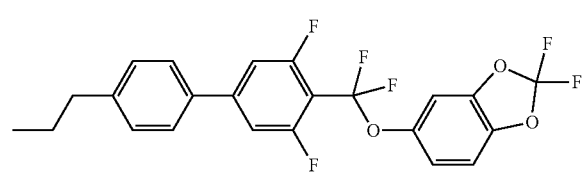 [SMILES: CCCc1ccc(-c2cc(F)c(C(F)(F)Oc3ccc4c(c3)OC(F)(F)O4)c(F)c2)cc1]

Firstly, 18.96 g (0.08 mol) of Compound 1 (5-Bromo-2, 2-difluorobenzodioxol), 1.52 g (0.008 mol) of CuI, 26.88 g (0.48 mol) of KOH, 200 mL of polyethylene glycol (PEG 400), and 50 mL of water were added into a reaction bottle. Then, the mixture in the reaction bottle was heated to reflux under nitrogen for 48 hours. After the reaction completed, an extraction was performed by using ethyl acetate (EA)/sodium chloride aqueous solution. The organic phase of the extraction solution was collected and concentrated. A column chromatography was performed by using hexane/EA (hexane:EA=8:2) as a mobile phase. The mobile phase after column chromatography was concentrated by the rotary concentrator, and Compound 2 (light yellow liquid) was obtained. The reaction is as follows:

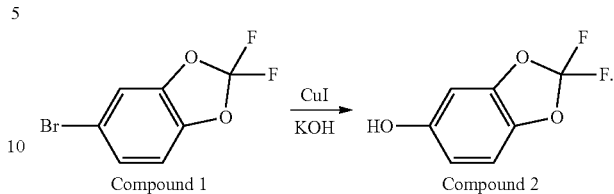

Then, 5.22 g (0.03 mol) of Compound 2, 7.11 g (0.03 mol) of Compound 3 (4-Bromo-2,6-difluorobenzoic acid), 4.5 g (0.03 mol) of trifluoromethanesulfonate, and 200 mL of toluene were added into a reaction bottle. Then, the mixture in the reaction bottle was heated to reflux under nitrogen for 48 hours. After the reaction completed, an extraction was performed by using ethyl acetate (EA)/sodium chloride aqueous solution. The organic phase of the extraction solution was collected and concentrated. A column chromatography was performed by using hexane as a mobile phase. The mobile phase after column chromatography was concentrated by the rotary concentrator, and Compound 4 (yellow oil) was obtained. The structure unit A3 of the final product may be changed by using different Compound 3 (such as,

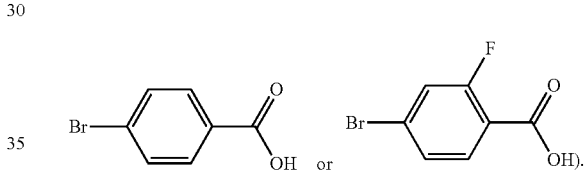

The reaction is as follows:

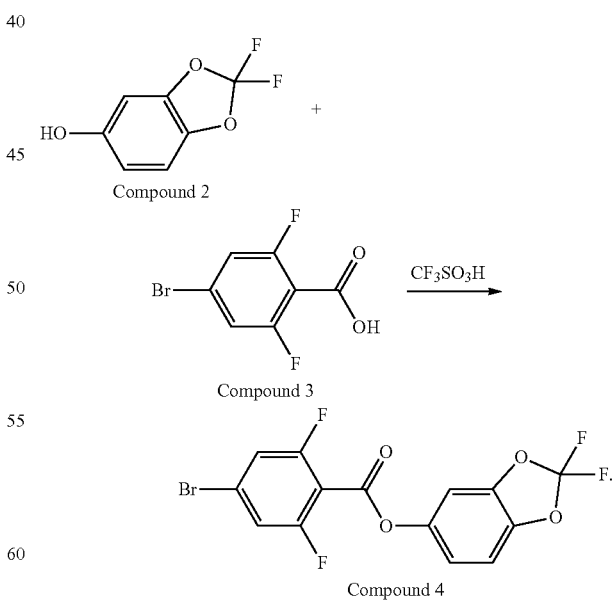

Then, 9.83 g (0.025 mol) of Compound 4, 20.2 g (0.05 mol) of Lawesson's reagent (2,4-bis(4-methoxyphenyl)-1, 3-dithia-2,4-diphosphetane-2,4-disulfide), and 100 mL of toluene were added into a reaction bottle. Then, the mixture in the reaction bottle was heated to reflux under nitrogen for 48 hours. After the reaction completed, an extraction was performed by using ethyl acetate (EA)/sodium chloride aqueous solution. The organic phase of the extraction solution was collected and concentrated. A column chromatography was performed by using hexane as a mobile phase. The mobile phase after column chromatography was concentrated by the rotary concentrator, and Compound 5 (yellow oil) was obtained. The reaction is as follows:

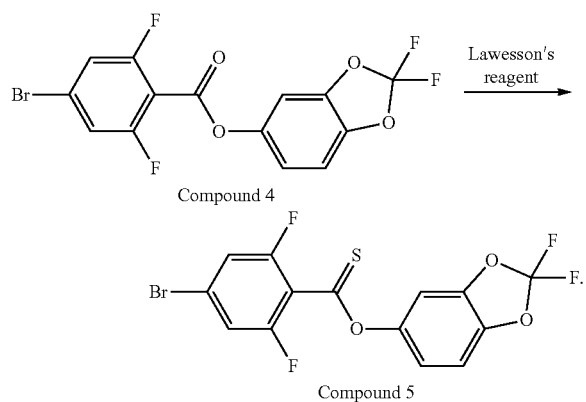

Then, 8.18 g (0.02 mol) of Compound 5 and 100 mL of dichloromethane were added into a reaction bottle. The mixture in the reaction bottle was cooled down to 0° C. Then, 6.4 g (0.04 mol) of diethylaminosulfurtrifluoride (DAST) was slowly added into the reaction bottle under nitrogen and the mixture was stirred at 0° C. for 4 hours. Then, the mixture was stirred at room temperature for 10 hours. After stirring, the reaction was quenched by adding 10 mL of sodium chloride aqueous solution. Then, an extraction was performed by using ethyl acetate (EA)/I sodium chloride aqueous solution. The organic phase of the extraction solution was collected and concentrated. A column chromatography was performed by using hexane as a mobile phase. The mobile phase after column chromatography was concentrated by the rotary concentrator, and Compound 6 (yellow oil) was obtained. The reaction is as follows:

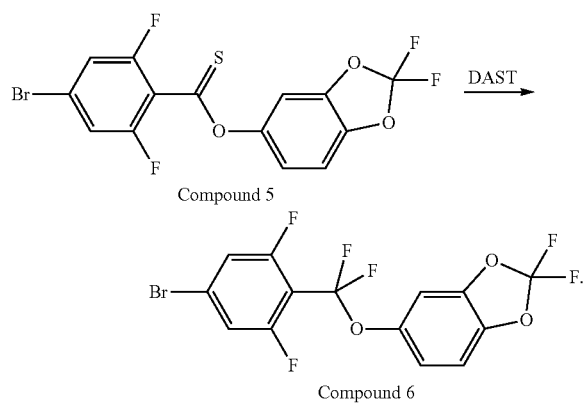

Then, 0.83 g (0.002 mol) of Compound 6, 0.33 g (0.002 mol) of Compound 7 (4-Propylphenylboronic acid), 0.552 g (0.004 mol) $K_2CO_3$, 50 mL of tetrahydrofuran (THF), and 5 mL of water were added into a reaction bottle. Then, 0.2 g of tetra(triphenylphosphine)palladium ($Pd[P(Ph)_3]_4$) was slowly added into the reaction bottle under nitrogen. Then, the mixture in the reaction bottle was heated to reflux under nitrogen for 48 hours. After the reaction completed, an extraction was performed by using ethyl acetate (EA)/ sodium chloride aqueous solution. The organic phase of the extraction solution was collected and concentrated. A column chromatography was performed by using hexane as a mobile phase. The mobile phase after column chromatography was concentrated by the rotary concentrator, and the crude product was obtained. Then, the crude product was recrystallized by using 20 mL of toluene and 50 mL anhydrous alcohol as the solvent, and Liquid Crystal Compound (a) (white solid) was obtained. The structure unit A2 of the final product may be changed by using different Compound 7 (such as,

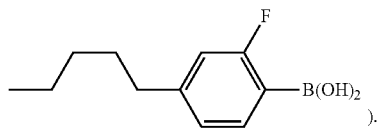

).

The reaction is as follows:

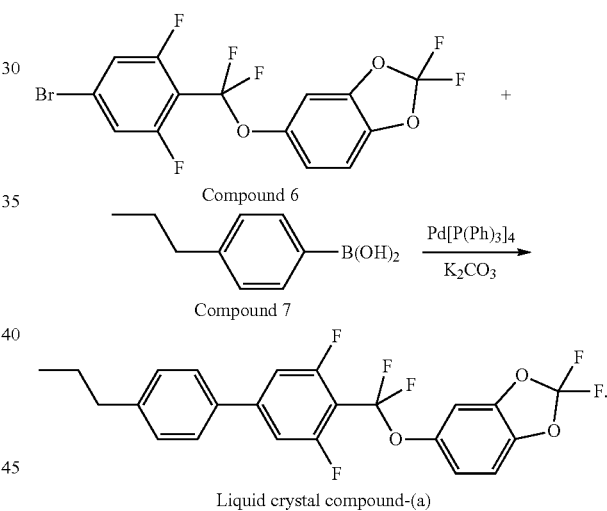

Then, Liquid Crystal Compound (a) was analyzed by using a nuclear magnetic resonance spectrometer (NMR), and the results were as follows: $^1$H NMR (400 MHz, $CDCl_3$): δ 7.46 (d, J=8.4 Hz, 2H), 7.27 (d, J=8 Hz, 2H), 7.19 (s, 1H), 7.16 (s, 1H), 7.06 (s, 1H), 7.01 (s, 2H), 2.62 (t, J=7.6 Hz, 2H), 1.66 (m, 2H), 0.95 (t, J=7.2 Hz, 2H).

Example 2 Liquid Crystal Compound (b)

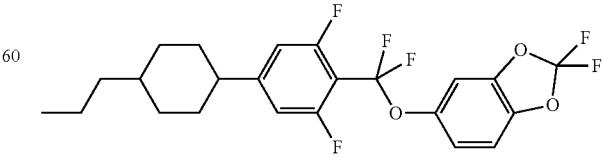

Firstly, 0.83 g (0.002 mol) of Compound 6 and 50 mL of THF were added into a reaction bottle and then cooled down to −78° C. Then, 2.5M (0.003 mol) of n-butyllithium (n-BuLi) was slowly added into the reaction bottle, and the mixture was stirred at −78° C. for 1 hour. Then, 0.28 g (0.002 mol) of Compound 8 (4-propyl-cyclohexanone) was slowly added into the reaction bottle, and the mixture was stirred at room temperature for 4 hour. Then, an extraction was performed by using ethyl acetate (EA)/sodium chloride aqueous solution. The organic phase of the extraction solution was collected and concentrated. A column chromatography was performed by using hexane as a mobile phase. The mobile phase after column chromatography was concentrated by the rotary concentrator, and Compound 9 (yellow oil) was obtained. The structure unit A2 of the final product may be changed by using different Compound 8 (such as,

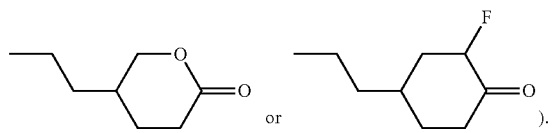

). The reaction is as follows:

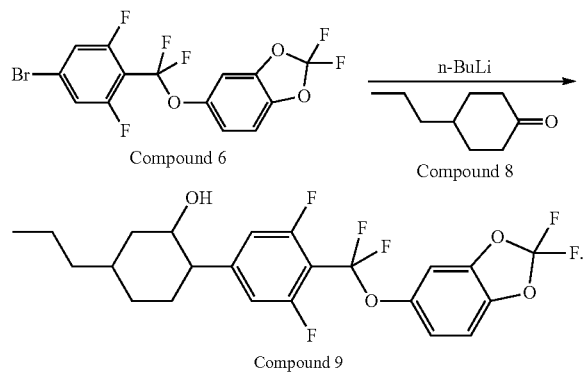

Then, 0.86 g (0.0018 mol) of Compound 9, 50 mL of toluene, and 0.342 g (0.0018 mol) of p-toluenesulfonic acid hydrate (TsOH) were added into a reaction bottle. Then, the mixture in the reaction bottle was heated to reflux under nitrogen for 48 hours. After the mixture was cooled to room temperature, an extraction was performed by using ethyl acetate (EA)/sodium chloride aqueous solution. The organic phase of the extraction solution was collected and concentrated. A column chromatography was performed by using hexane as a mobile phase. The mobile phase after column chromatography was concentrated by the rotary concentrator, and Compound 10 (yellow oil) was obtained. The reaction is as follows:

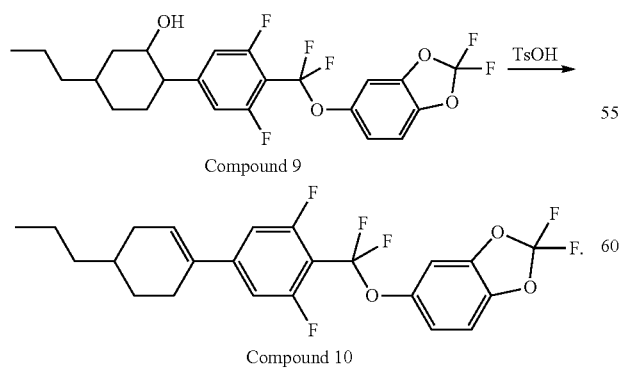

Then, 0.82 g (0.0018 mol) of Compound 10 and Pd/C catalyst (palladium 20% on carbon) were added into a reaction bottle. Then, 25 mL of methanol was slowly added into the reaction bottle under hydrogen, and the mixture was stirred at room temperature for 8 hour. Then, an extraction was performed by using ethyl acetate (EA), sodium chloride aqueous solution. The organic phase of the extraction solution was collected and concentrated. A column chromatography was performed by using hexane as a mobile phase. The mobile phase after column chromatography was concentrated by the rotary concentrator, and the crude product was obtained. Then, the crude product was recrystallized by using 20 mL of toluene and 50 mL anhydrous alcohol as the solvent, and Liquid Crystal Compound (b) (white solid) was obtained. The reaction is as follows:

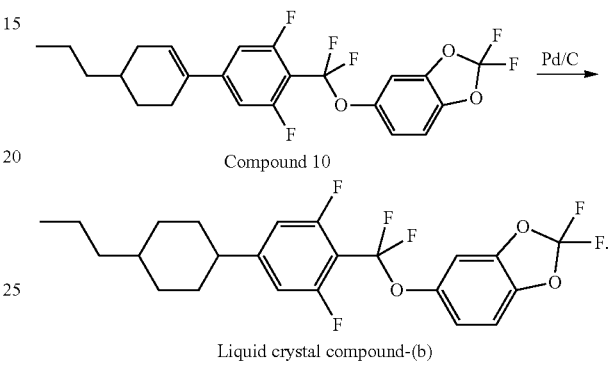

Then, Liquid Crystal Compound (b) was analyzed by using a nuclear magnetic resonance spectrometer (NMR), and the results were as follows: $^1$H NMR (400 MHz, CDCl$_3$): δ 7.04 (s, 1H), 6.99 (s, 2H), 6.81 (d, J=5.6 Hz, 2H), 2.46 (t, J=6, 1H), 1.86 (d, J=5.6 Hz, 4H), 1.41-0.81 (m, 12H).

Example 3 Liquid Crystal Compound (c)

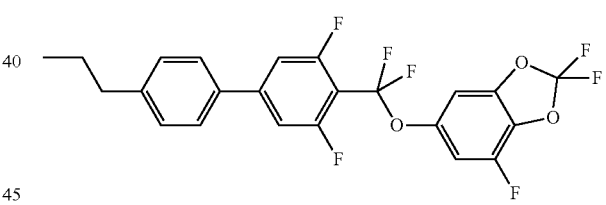

Firstly, 2.5 g (0.017 mol) of Compound 2, 3.0 g (0.020 mol) of tert-butyldimethylchlorosilane, 2.7 g (0.04 mol) of imidazole, and 100 mL of DMF were added into a reaction bottle. Then, the mixture in the reaction bottle was heated to 90° C. under nitrogen for 24 hours. Then, an extraction was performed by using ethyl acetate (EA)/sodium chloride aqueous solution. The organic phase of the extraction solution was collected and concentrated. A column chromatography was performed by using hexane as a mobile phase. The mobile phase after column chromatography was concentrated by the rotary concentrator, and Compound 12 (colorless liquid) was obtained. The reaction is as follows:

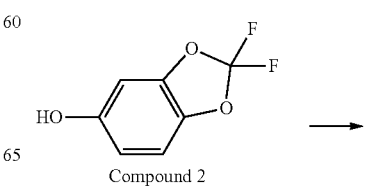

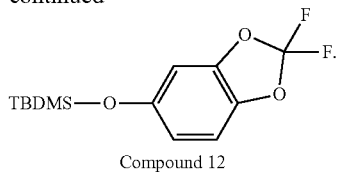

Compound 12

Then, 1.15 g (0.004 mol) of Compound 12 and 20 mL of THF were added into a reaction bottle and cooled down to −78° C. Then, 2.5M (2 mL) of n-butyllithium (n-BuLi) was slowly added into the reaction bottle, and the mixture was stirred at −78° C. for 1 hour. Then, a solution including 1.58 g (0.005 mol) of N-fluorobenzenesulfonimide and 1 mL THF was slowly added into the reaction bottle, and the mixture was stirred at −78° C. for 1 hour. Then, the mixture was stirred at room temperature for 2 hour. After the reaction completed, HCl was added until the solution becoming acidic. Then, an extraction was performed by using ethyl acetate (EA)/sodium chloride aqueous solution. The organic phase of the extraction solution was collected and concentrated. A column chromatography was performed by using hexane as a mobile phase. The mobile phase after column chromatography was concentrated by the rotary concentrator, and Compound 13 (colorless oil) was obtained. The reaction is as follows:

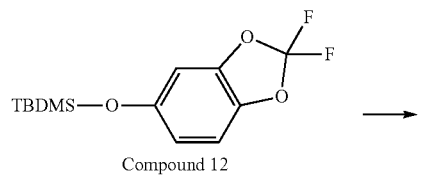

Compound 12

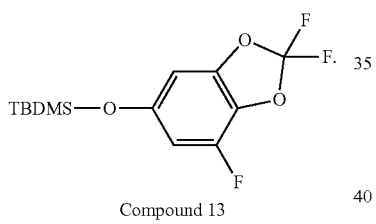

Compound 13

Then, 1.22 g (0.004 mol) of Compound 13, 0.336 g (0.006 mol) of KOH, and 100 mL of ethanol were added into a reaction bottle, and the mixture was stirred at room temperature for 4 hour. Then, HCl was slowly added until the solution becoming acidic. Then, an extraction was performed by using ethyl acetate (EA)/sodium chloride aqueous solution. The organic phase of the extraction solution was collected and concentrated. A column chromatography was performed by using hexane/EA (hexane:EA=8:2) as a mobile phase. The mobile phase after column chromatography was concentrated by the rotary concentrator, and Compound 14 (colorless oil) was obtained. The reaction is as follows:

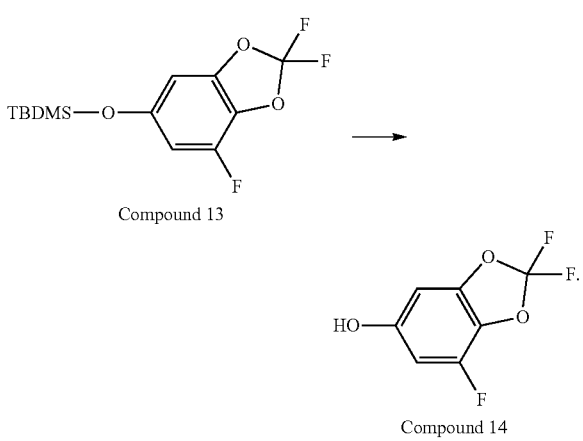

Then, the steps for synthesizing Liquid Crystal Compound (c) by Compound 14 are the same as the steps for synthesizing Liquid Crystal Compound (a) by Compound 2, expect that Compound 2 was replaced by Compound 14. For the purpose of simplicity and clarity, the detailed will not be repeated here.

Then, Liquid Crystal Compound (c) was analyzed by using a nuclear magnetic resonance spectrometer (NMR), and the results were as follows: $^1$H NMR (400 MHz, CDCl$_3$): δ 7.47 (d, J=8.4 Hz, 2H), 7.27 (d, J=8 Hz, 2H), 7.20 (s, 1H), 7.18 (s, 1H), 6.91 (s, 1H), 6.88 (s, 1H), 2.62 (t, J=7.6 Hz, 2H), 1.66 (m, 2H), 0.95 (t, J=7.2 Hz, 2H).

Comparative Examples

For comparing the properties, the comparative examples of liquid crystal compounds as shown in Table 2 were prepared.

TABLE 2

| code | Chemical structure |
|---|---|
| Liquid Crystal Compound (d) | 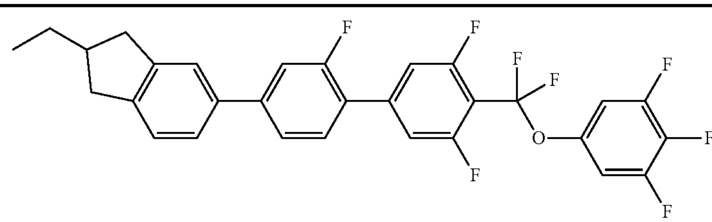 |
| Liquid Crystal Compound (e) | 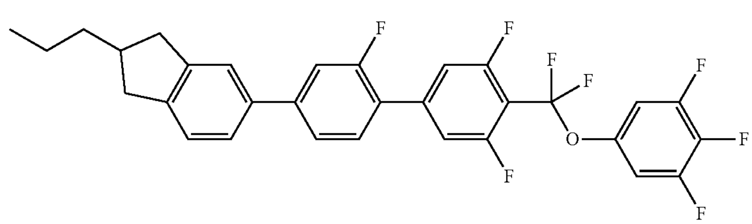 [SMILES: CCCC1Cc2ccc(-c3ccc(-c4cc(F)c(C(F)(F)Oc5cc(F)c(F)c(F)c5)c(F)c4)c(F)c3)cc2C1] |

TABLE 2-continued

| code | Chemical structure |
|---|---|
| Liquid Crystal Compound (f) | 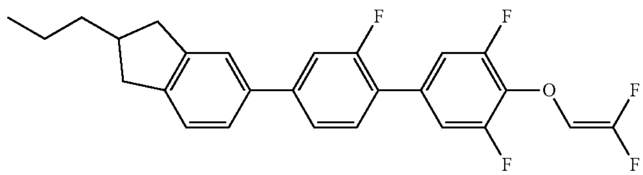 [SMILES: CCCC1Cc2ccc(-c3ccc(-c4cc(F)c(OC=C(F)F)c(F)c4)c(F)c3)cc2C1] |
| Liquid Crystal Compound (g) | 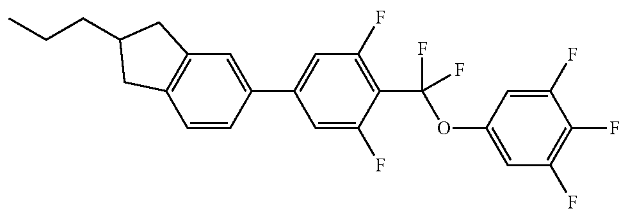 [SMILES: CCCC1Cc2ccc(-c3cc(F)c(C(F)(F)Oc4cc(F)c(F)c(F)c4)c(F)c3)cc2C1] |
| Liquid Crystal Compound (h) | 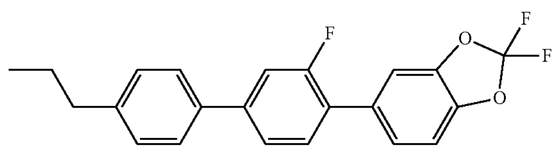 [SMILES: CCCc1ccc(-c2ccc(-c3ccc4c(c3)OC(F)(F)O4)c(F)c2)cc1] |
| Liquid Crystal Compound (i) | 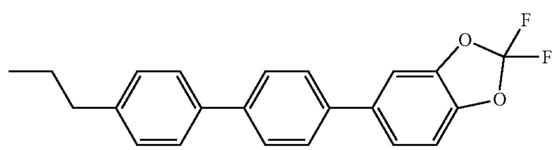 [SMILES: CCCc1ccc(-c2ccc(-c3ccc4c(c3)OC(F)(F)O4)cc2)cc1] |
| Liquid Crystal Compound (j) | 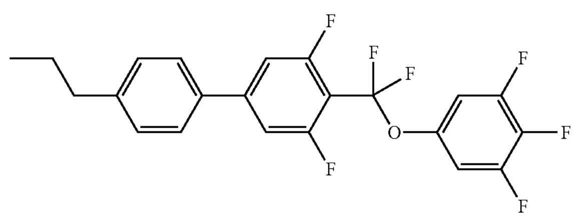 [SMILES: CCCc1ccc(-c2cc(F)c(C(F)(F)Oc3cc(F)c(F)c(F)c3)c(F)c2)cc1] |
| Liquid Crystal Compound (k) | 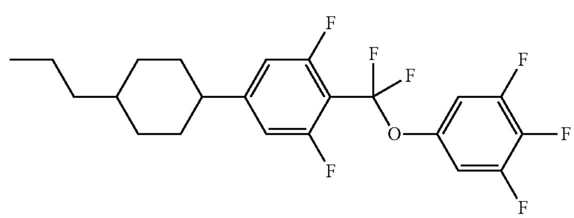 [SMILES: CCCC1CCC(c2cc(F)c(C(F)(F)Oc3cc(F)c(F)c(F)c3)c(F)c2)CC1] |

The Liquid Crystal Compound (a), Liquid Crystal Compound (c) and liquid Crystal Compounds shown in Table 2 were directly mixed with mother liquor. The properties of these liquid crystal compounds were measured and calculated by extrapolation method. The experimental results are shown in Tables 3-5.

Refractive Anisotropy (Δn)

The main prism was wiped along a direction, and a small amount of the liquid crystal compound was dropped onto the main prism. The measurement was performed at 25° C., using a wavelength of 598 nm filter, by the Abbe refractometer having a polarizing plate on its eyepiece. When the polarization direction was parallel to the direction of wiping, the refractive index was measured as n∥; when wiping direction was perpendicular to the polarization direction, the refractive index was measured as n⊥. Refractive index anisotropy (Δn) is equal to the difference value between n∥ and n⊥.

Dielectric Anisotropy (Δε)

The liquid crystal compound was loaded into a liquid crystal cell having an average interval of 9 μm. The voltage of 20V to 50V was applied to the liquid crystal cell at 25° C. The average dielectric constant along the direction parallel to the major axis of the liquid crystal molecules was measured as ε∥; and the average dielectric constant along the direction perpendicular to the major axis of the liquid crystal molecules was measured as ε⊥. Dielectric anisotropy (Δε) is equal to the absolute value of the difference value between ε∥ and ε⊥.

Rotational Viscosity Coefficient (γ1)

The liquid crystal compound was loaded into a liquid crystal cell having an average interval of 9 μm. The voltage of 20V was applied to the liquid crystal cell at 25° C. Rotational viscosity (γ1) was calculated by the instrument adding the factor of dielectric anisotropy (Δε).

The properties of Liquid Crystal Compounds (a), (c) and (d)-(g) are shown in Table 3.

TABLE 3

| | Liquid Crystal Compound | | | | | |
|---|---|---|---|---|---|---|
| | (a) | (c) | (d) | (e) | (f) | (g) |
| Δ ε | 18.09 | 21.01 | 25.15 | 24.53 | 14.57 | 19.42 |
| Δn | 0.1310 | 0.1287 | 0.1963 | 0.1962 | 0.1964 | 0.1194 |
| γ1 (unit: mPa · s) | 63.11 | 50.13 | 181.02 | 183.98 | 183.98 | 94.54 |
| γ1/Δ ε | 3.49 | 2.39 | 7.20 | 7.50 | 10.96 | 4.87 |

As shown in Table 3, the Δn values of Liquid Crystal Compounds (a) and (c) were both in the required range of the Δn value (in a range of 0.10-0.20) for liquid crystal display, and the rotational viscosity values of Liquid Crystal Compounds (a) and (c) were both smaller than those of Liquid Crystal Compounds (d)-(g). Furthermore, for Liquid Crystal Compounds (a) and (c), the ratio values of rotational viscosity coefficient to dielectric anisotropy (i.e., γ1/Δε) were both smaller than 4. Therefore, in comparison with Liquid Crystal Compounds (d)-(g), Liquid Crystal Compounds (a) and (c) had higher response speed.

The properties of Liquid Crystal Compounds (a), (c) and (h)-(i) are shown in Table 4.

TABLE 4

| Liquid Crystal Compound | (a) | (c) | (h) | (i) |
|---|---|---|---|---|
| Δ ε | 18.09 | 21.01 | 12.29 | 10.15 |
| Δn | 0.1310 | 0.1287 | 0.224 | 0.2659 |
| γ1 unit: mPa · s | 63.11 | 50.13 | 131.3 | 120.0 |
| γ1/Δ ε | 3.49 | 2.39 | 10.68 | 11.82 |

As shown in Table 4, the Δε values of Liquid Crystal Compounds (a) and (c) were both greater than those of Liquid Crystal Compounds (h)-(i). Therefore, when Liquid Crystal Compounds (a) and (c) are used in a liquid crystal display, a lower driving voltage will be obtained. Furthermore, the rotational viscosity values of Liquid Crystal Compounds (a) and (c) were both smaller than those of Liquid Crystal Compounds (h)-(i), and the γ1/Δε values of Liquid Crystal Compounds (a) and (c) values were both much smaller than those of Liquid Crystal Compounds (h)-(i). Therefore, in comparison with Liquid Crystal Compounds (h)-(i), Liquid Crystal Compounds (a) and (c) had higher response speed.

The properties of Liquid Crystal Compounds (a), (c) and (j)-(k) are shown in Table 5.

TABLE 5

| Liquid Crystal Compound | (a) | (c) | (j) | (k) |
|---|---|---|---|---|
| Δ ε | 18.09 | 21.01 | 21.32 | 13.37 |
| Δn | 0.1310 | 0.1287 | 0.1213 | 0.0599 |
| γ1 unit: mPa · s | 63.11 | 50.13 | 36.99 | 33.13 |
| γ1/Δ ε | 3.49 | 2.39 | 1.74 | 2.48 |

As shown in Table 5, the Δn values of Liquid Crystal Compounds (a) and (c) were both greater than Liquid Crystal Compounds (j)-(k).

The Δn and Δε values of Liquid Crystal Compounds (a) and Liquid Crystal Compounds (1) (3PPQIof) were simulated and calculated by using molecular orbital calculation software (MOPAC 2000, Fujitsu Ltd.) and Maier Meier equation. The simulation results are shown in Table 6. Simulating and calculating methods of the Δn values and the Δε values were as follows. Firstly, the more stable molecular structure was determined by optimization of energy, and then, the stable configurations of liquid crystal molecules were calculated by software MOPAC (software MOPAC obtained molecular information by using semi-empirical rules, and the chosen model was PM6). After the stable configurations of liquid crystal molecules were obtained, polarizability, dipole moment, and the ratio of main axis and minor axis were calculated. Finally, these information were set into the Maier-Meier equation, and then, the an and as values were obtained.

TABLE 6

| Liquid Crystal Compound | (a) | (l) |
|---|---|---|
| Δ ε | 20.186 | 14.138 |
| Δn | 0.0912 | 0.0639 |
| γ1 | 229.4057 | 390.4228 |

The difference between Liquid Crystal Compounds (a) and (l) was that Liquid Crystal Compound (a) has two hydrogen atoms at 2,6 positions of the central benzene ring substituted by fluorine atoms. As shown in Table 6, when hydrogen atoms at 2,6 positions of the central benzene ring were substituted by fluorine atoms, the Δn and Δε values of Liquid Crystal Compound (a) were significantly increased.

Example 4 Liquid Crystal Composition

The liquid crystal composition of Example 4 was obtained by directly mixing Liquid Crystal Compound (a) and the liquid crystal compounds represented by Formula (II). Similarly, the liquid crystal composition of Reference Example 1 was obtained directly mixing the liquid crystal compounds represented by Formula (II). The liquid crystal compounds and the corresponding content for Example 4 and Reference Example 1 are shown in Table 7.

TABLE 7

| | Example 4 | Reference Example 1 |
|---|---|---|
| 2CCGF | 30.0 wt % | 33.3 wt % |
| 3CCGF | 30.0 wt % | 33.3 wt % |
| 5CCGF | 30.0 wt % | 33.3 wt % |
| Liquid Crystal Compound (a) | 10.0 wt % | 0 wt % |

Example 5 Liquid Crystal Composition

Similarly, the liquid crystal composition of Example 5 and Reference Example 2 were obtained by directly mixing the liquid crystal compounds. The liquid crystal compounds and the corresponding content for Example 5 and Reference Example 2 are shown in Table 8.

TABLE 8

| | Example 5 | Reference Example 2 |
|---|---|---|
| 3CCV | 47.21 wt % | 50.24 wt % |
| 5PP1 | 11.77 wt % | 12.54 wt % |
| 3CPTP2 | 11.62 wt % | 12 38 wt % |
| 3CPP2 | 7.40 wt % | 7.89 wt % |
| 3RIGU-O2F | 6.34 wt % | 6.75 wt % |
| 2CPPF | 9.66 wt % | 10.29 wt % |
| Liquid Crystal Compound (c) | 6.00 wt % | 0 wt % |

The properties of these liquid crystal compositions were measured and calculated by the same method as described above. For the purpose of simplicity and clarity, the detailed will not be repeated here. The experimental results are shown in Table 9.

TABLE 9

| | Example 4 | Reference Example 1 | Example 5 | Reference Example 2 |
|---|---|---|---|---|
| Δε | 7.11 | 5.88 | 2.36 | 1.48 |
| Δn | 0.085 | 0.079 | 0.1147 | 0.1156 |
| γ1 | 148 | 152 | 42 | 41.4 |

As shown in Table 9, when Liquid Crystal Compound (a) was added, the Δn and Δε values of the liquid crystal composition were significantly increased, and the γ1 value was reduced. Therefore, the response speed of the liquid crystal composition was improved. Furthermore, as shown in Table 9, when Liquid Crystal Compound (c) was added, the Δε values of the liquid crystal composition was significantly increased. Therefore, the driving voltage and energy consumption of the liquid crystal display having the liquid crystal composition is reduced.

Example 6-10 Liquid Crystal Composition

The liquid crystal compositions of Examples 6-10 were obtained by directly mixing the first component, the third component, and the fourth component described above. Similarly, the liquid crystal compositions of Reference Examples 3-7 were obtained directly mixing the liquid crystal compounds. The liquid crystal compounds for Examples 6-10 and Reference Examples 3-7 are shown in Table 10.

TABLE 10

| | Code name | Chemical structure |
|---|---|---|
| first component | 3CPIof | 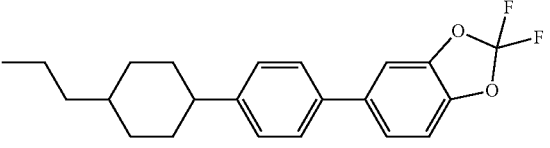 [SMILES: CCCC1CCC(c2ccc(-c3ccc4c(c3)OC(F)(F)O4)cc2)CC1] |
| | 3PPIof | 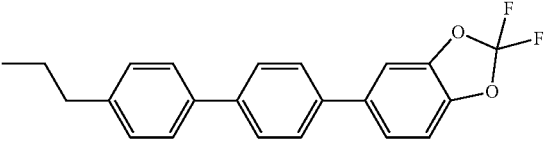 [SMILES: CCCc1ccc(-c2ccc(-c3ccc4c(c3)OC(F)(F)O4)cc2)cc1] |
| | 3PUQIof | 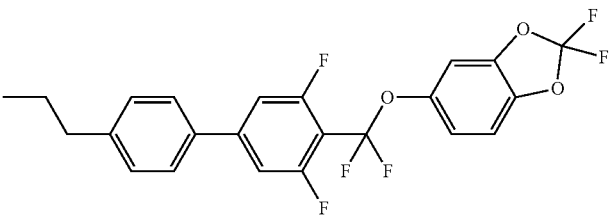 [SMILES: CCCc1ccc(-c2cc(F)c(C(F)(F)Oc3ccc4c(c3)OC(F)(F)O4)c(F)c2)cc1] |
| third component | 5toUQU-O$_2$F | 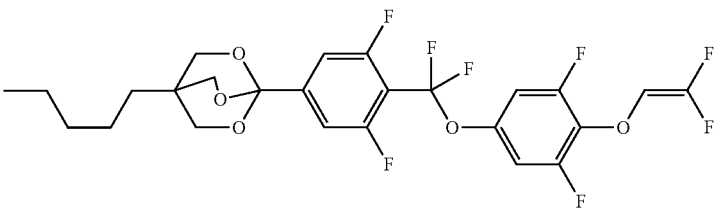 [SMILES: CCCCCC12COC(c3cc(F)c(C(F)(F)Oc4cc(F)c(OC=C(F)F)c(F)c4)c(F)c3)(OC1)OC2] |

TABLE 10-continued

| Code name | Chemical structure |
|---|---|
| 2toUQU-O₂F | |
| RIGUQUF | 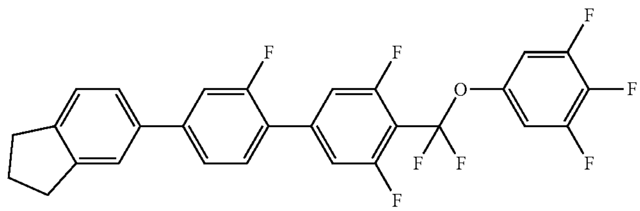 [SMILES: Fc1cc(-c2ccc3c(c2)CCC3)ccc1-c1cc(F)c(C(F)(F)Oc2cc(F)c(F)c(F)c2)c(F)c1] |
| 1RIGUQUF | 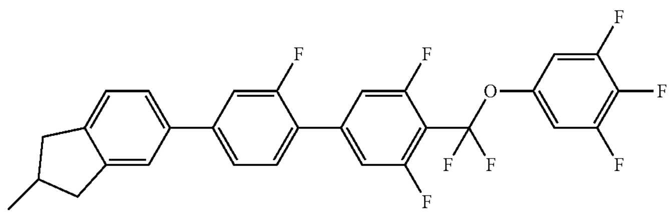 [SMILES: CC1Cc2ccc(-c3ccc(-c4cc(F)c(C(F)(F)Oc5cc(F)c(F)c(F)c5)c(F)c4)c(F)c3)cc2C1] |
| 2RIGUQUF | 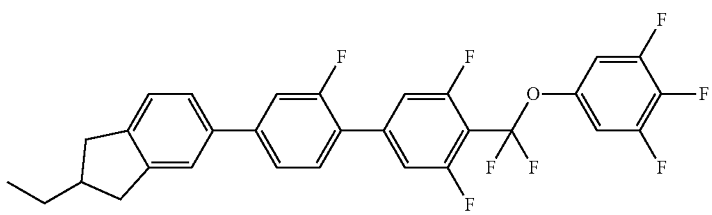 [SMILES: CCC1Cc2ccc(-c3ccc(-c4cc(F)c(C(F)(F)Oc5cc(F)c(F)c(F)c5)c(F)c4)c(F)c3)cc2C1] |
| 2RIGUQU-O₂F | |
| 3RIGUQUF | 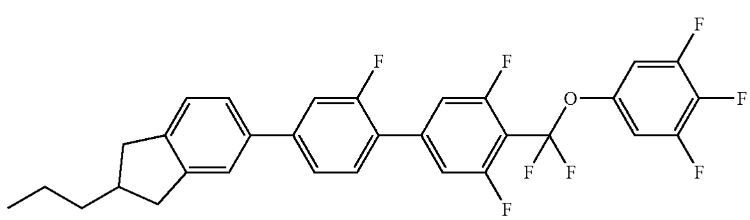 [SMILES: CCCC1Cc2ccc(-c3ccc(-c4cc(F)c(C(F)(F)Oc5cc(F)c(F)c(F)c5)c(F)c4)c(F)c3)cc2C1] |
| 3PUQUF | 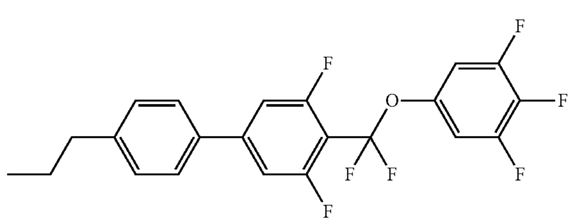 [SMILES: CCCc1ccc(-c2cc(F)c(C(F)(F)Oc3cc(F)c(F)c(F)c3)c(F)c2)cc1] |

TABLE 10-continued
| | Code name | Chemical structure |
|---|---|---|
| fourth component | 3CCV | 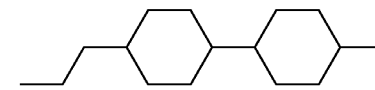 |
| | 3CC4 | 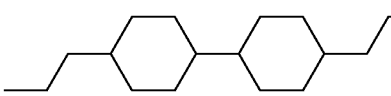 |
| | 3CC5 | 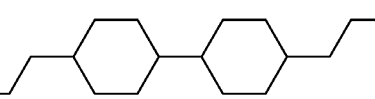 |
| | 3CCV1 | 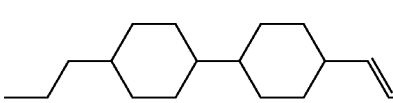 |
| | 5PP1 | 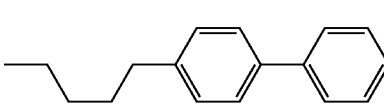 |
| | 1PTPO2 |  |
| | 3CPTP2 | 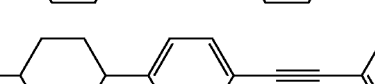 |
| | 3CPTP4 | 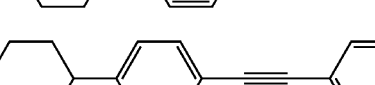 |
| | V2PTP2V | 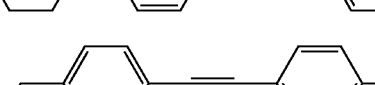 |
| | 2CPGF |  |
| | 3CPGF | 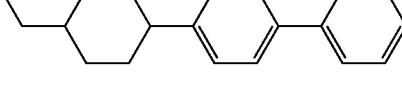 |
| | 3CCPOCF$_3$ | 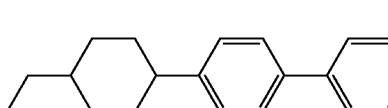 |
| | 2CPPF | 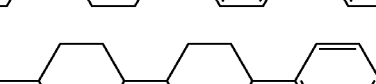 |
| | 3CPPF | 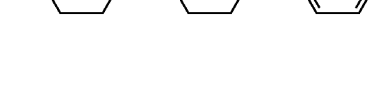 |

TABLE 10-continued

| Code name | Chemical structure |
|---|---|
| 2CCPUF | 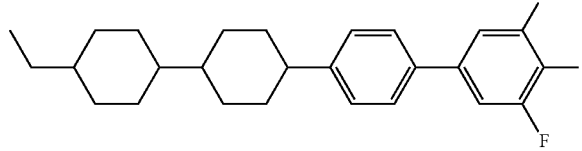 |
| 3CCGUF | 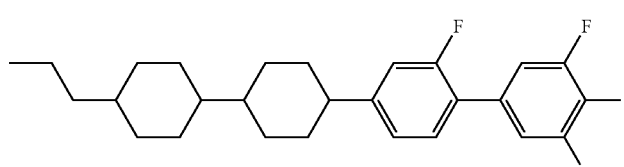 |
| 3PGUF | 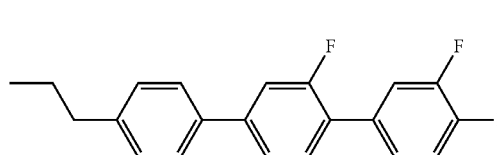 |
| 3CPUF | 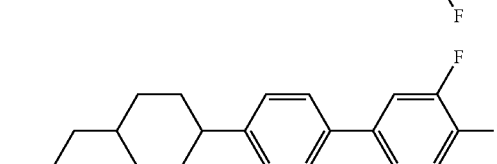 |

Manufacturing methods of the first component are described as follows. In the disclosure, the liquid crystal compound 3PUQIof is an example for explaining the manufacturing method of the liquid crystal compound having Z4 is —CF$_2$O— or —OCF$_2$—: the liquid crystal compound 3PPIof is an example for explaining the manufacturing method of the liquid crystal compound having Z4 is not —CF$_2$O— or —OCF$_2$—. The manufacturing method of liquid crystal compound 3PUQIof (i.e., Liquid Crystal Compound (a)) have been described above. For the purpose of simplicity and clarity, the detailed will not be repeated here.

Manufacturing Method of Liquid Crystal Compound 3PPIof

Firstly, 3.55 g (0.015 mol) of Compound 1, 10.8 g (0.045 mol) of Compound 15 (4'-propyl-biphenyl-4-yl) boronic acid, 16.584 g (0.12 mol) of K$_2$CO$_3$, 50 mL of THF, and 5 mL of water were added into a reaction bottle. Then, 0.2 g of tetra(triphenylphosphine)palladium (Pd[P(Ph)$_3$]4) was slowly added into the reaction bottle under nitrogen. Then, the mixture in the reaction bottle was heated to reflux under nitrogen for 48 hours. After the reaction completed, an extraction was performed by using ethyl acetate (EA)/sodium chloride aqueous solution. The organic phase of the extraction solution was collected and concentrated. A column chromatography was performed by using hexane as a mobile phase. The mobile phase after column chromatography was concentrated by the rotary concentrator, and the crude product was obtained. Then, the crude product was recrystallized by using 20 mL of toluene and 50 mL anhydrous alcohol as the solvent, and liquid crystal compound 3PPIof(white solid) was obtained. The final product may be changed by using different Compound 15 (such as, 2PPIof may be obtained by choosing (4'-ethyl-biphenyl-4-yl) boronic acid as Compound 15). The reaction is as follows:

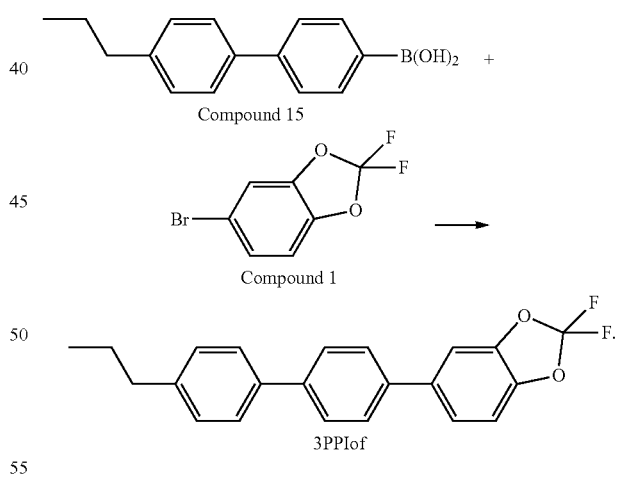

Manufacturing methods of the third component are described in U.S. Pat. No. 8,388,861 B2 (Taiwan Patent No. TWI462993 B), the entirety of which is incorporated by reference. The fourth component is commercial product.

The content and properties of the liquid crystal compositions of Examples 6-10 and Reference Examples 3-7 are shown in Table 11. In Table 11, Examples are E-6, E-7-1, E-7-2, E-8-1, E-8-2, E-9-1, E-9-2, and E-10; Reference Examples are R-3, R-4, R-5, R-6, R-7-1, and R-7-2. Furthermore, the unit of the content is wt % (based on a total weight of the liquid crystal composition).

TABLE 11

|  | R-3 | E-6 | R-4 | E-7-1 | E-7-2 | R-5 | E-8-1 | E-8-2 |
|---|---|---|---|---|---|---|---|---|
| first component | | | | | | | | |
| 3CPIof | | | | 5.3 | 5.3 | | 7 | 7 |
| 3PPIof | | 2.5 | | | | | | |
| 3PUQIof | | | | | 6.2 | | | |
| third component | | | | | | | | |
| 5toUQU-$O_2$F | | | | | | | | |
| 2toUQU-$O_2$F | 4 | 4 | 4.5 | | 6.2 | 4.5 | 7 | |
| RIGUQUF | 4.5 | 4.5 | 4 | 4 | 4 | 4 | 4 | 4 |
| 1RIGUQUF | 4.5 | 4.5 | 4 | 4 | 4 | 4 | 5 | 4 |
| 2RIGUQUF | 4 | 4 | 4 | 4 | 4 | 4 | | 4 |
| 2RIGUQU-$O_2$F | | | | | | | | |
| 3RIGUQUF | 4 | 4 | 5 | 5 | 5 | 5 | 5 | 5 |
| 3PUQUF | | | | | | | | 4.5 |
| fourth component | | | | | | | | |
| 3CCV | 43 | 43 | 42.5 | 42.5 | 42.5 | 42.5 | 40.5 | 42.5 |
| 3CC4 | | | 2 | | 2 | | 8 | 2 |
| 3CC5 | | | | 2 | | 2 | | |
| 3CCV1 | 2.1 | 2.1 | | | | | | |
| 5PP1 | | | | | | | | |
| 1PTPO2 | | | 3 | 3 | 3 | 3 | | 3 |
| 3CPTP2 | 4 | 4 | 7.4 | 7.4 | 7.4 | 7.4 | 7.4 | 7.4 |
| 3CPTP4 | 3.4 | 3.4 | | | | | | |
| V2PTP2V | 11.6 | 11.6 | 8.6 | 8.6 | 8.6 | 8.6 | 8.6 | 8.6 |
| 2CPGF | | | | | | | 7 | |
| 3CPGF | 2.5 | | | | | | | |
| 3CCPOCF$_3$ | 12.4 | 12.4 | 5.5 | 5.5 | 5.5 | 5.5 | 7.5 | 5.5 |
| 2CPPF | | | | | | | | |
| 3CPPF | | | 2.5 | 2.5 | 2.5 | 2.5 | | 2.5 |
| 2CCPUF | | | | | | | | |
| 3CCGUF | | | | | | | | |
| 3PGUF | | | | | | | | |
| 3CPUF | | | 7 | | | | | |
| TOTAL (wt %) | 100 | 100 | 100 | 100 | 100 | 100 | 100 | 100 |
| Content of first component (wt %) | 0 | 2.5 | 0 | 11.5 | 5.3 | 0 | 7 | 7 |
| Content of third component (wt %) | 21 | 21 | 21.5 | 17 | 23.2 | 21.5 | 21 | 21.5 |
| Δ∈ | 5.99 | 6.18 | 6.60 | 6.00 | 6.60 | 6.52 | 6.44 | 5.80 |
| K11 | 9.57 | 10.10 | 9.18 | 11.10 | 9.45 | 9.10 | 9.25 | 9.99 |
| γ1 | 49.43 | 51.07 | 50.35 | 60.00 | 49.97 | 51.61 | 52.09 | 52.42 |
| γ1/K11 | 5.1651 | 5.0564 | 5.4848 | 5.4054 | 5.2878 | 5.6714 | 5.6314 | 5.2472 |

|  | R-6 | E-9-1 | E-9-2 | R-7-1 | R-7-2 | E-10 |
|---|---|---|---|---|---|---|
| first component | | | | | | |
| 3CPIof | | 8.5 | 5.3 | | | 4 |
| 3PPIof | | | | 2 | | 2 |
| 3PUQIof | | | 2 | | | |
| third component | | | | | | |
| 5toUQU-$O_2$F | | | 4.2 | | | |
| 2toUQU-$O_2$F | | 9.5 | | | | |
| RIGUQUF | 2 | | 6 | | | |
| 1RIGUQUF | 2 | | 4 | | | |
| 2RIGUQUF | 6 | | 2 | | 7 | 7 |
| 2RIGUQU-$O_2$F | | 4 | | | | |
| 3RIGUQUF | 7 | 6 | 3 | | 4 | 4 |
| 3PUQUF | 4.5 | | | | | |
| fourth component | | | | | | |
| 3CCV | 38.5 | 37.5 | 43.5 | 40.6 | 40.6 | 40.6 |
| 3CC4 | 6 | 11 | | | | |
| 3CC5 | | | 3 | | | |
| 3CCV1 | | | | 4 | 4 | 4 |
| 5PP1 | | | | 11.1 | 11.1 | 11.1 |
| 1PTPO2 | 3.4 | | 4 | | | |
| 3CPTP2 | 6.5 | 7.4 | 7.4 | 11 | 11 | 11 |
| 3CPTP4 | | | | | | |
| V2PTP2V | 9.1 | 8.6 | 7.6 | | | |
| 2CPGF | | | | | | |
| 3CPGF | | | | 7 | 7 | 7 |
| 3CCPOCF$_3$ | 2.5 | 7.5 | 5.5 | | | |
| 2CPPF | | | | 4 | 4 | 4 |

TABLE 11-continued

| | | | | | | |
|---|---|---|---|---|---|---|
| 3CPPF | 5.5 | | 2.5 | 5 | 5 | 5 |
| 2CCPUF | | | | 7 | | |
| 3CCGUF | | | | 4 | | |
| 3PGUF | | | | 4 | 6 | |
| 3CPUF | 7 | | | | | |
| TOTAL (wt %) | 100 | 100 | 100 | 100 | 100 | 100 |
| Content of first component (wt %) | 0 | 8.5 | 7.3 | 2 | 0 | 6 |
| Content of third component (wt %) | 21.5 | 19.5 | 19.2 | 0 | 11 | 11 |
| Δε | 5.86 | 6.23 | 5.94 | 2.50 | 3.70 | 3.37 |
| K11 | 9.50 | 9.54 | 9.77 | 12.20 | 11.30 | 11.90 |
| γ1 | 51.30 | 50.72 | 52.30 | 51.70 | 54.20 | 47.60 |
| γ1/K11 | 5.4000 | 5.3166 | 5.3531 | 4.2377 | 4.7965 | 4.0000 |

Referring to Reference Examples R-3 and Example E-6 in Table 11, Example E-6 included the first component 3PPIof having the structure unit Iof and Reference Examples R-3 did not include the first component. As shown in Table 11, because of the structure unit Iof, the liquid crystal composition had higher Δε value and lower γ1/K11 value. In other words, because of the first component, the liquid crystal composition had higher response speed and lower energy consumption.

Referring to Reference Examples R-4 and Example E-7-1 and E-7-2 in Table 11, similarly, Example E-7-1 and E-7-2 had higher Δε value and lower γ1/K11 value because of the first component. Furthermore, referring to Example E-7-1 and E-7-2 in Table 11, Example E-7-1 included the first component 3PUQIof having the structure unit QIof, and Example E-7-2 did not include the first component having the structure unit QIof. As shown in Table 11, the structure unit QIof significantly increased the K11 value. Therefore, the elastic coefficient of the liquid crystal composition may be tailored by adjusting the content of the first component having the structure unit QIof.

Referring to Reference Examples R-5 and Example E-8-1 and E-8-2 in Table 11, similarly, Example E-8-1 and E-8-2 had higher Δε value and lower γ1/K11 value because of the first component. Furthermore, referring to Example E-8-1 and E-8-2 in Table 11, Example E-8-1 included the third component 2toUQUO$_2$ f having the structure unit to, and Example E-8-2 included the third component 3PUQUIof having the structure unit P. As shown in Table 11, the structure unit to increased the Δε value, and the structure unit P increased the K11 value. Therefore, the Δε and K11 value of the liquid crystal composition may be tailored by adjusting the structure unit and the content of the third component.

Referring to Reference Examples R-6 and Example E-9-1 and E-9-2 in Table 11, similarly, Example E-9-1 and E-9-2 had higher Δε value and lower γ1/K11 value because of the first component. Furthermore, referring to Example E-91 and E-9-2 in Table 11, the content of the first component of Example E-9-1 (8.5 wt %) was greater than that of Example E-9-2 (7.3 wt %). As shown in Table 11, because of the increased content of the first component, the γ1 and γ1/K11 value were reduced. Therefore, the Δε and γ1 values of the liquid crystal composition may be tailored in a desired range by adjusting the content of the first component.

Referring to Reference Examples R-7-1 and Example E-10 in Table 11. Example E-10 included both the first component and the third component, and Reference Examples R-7-1 only included the first component. As shown in Table 11, the Δε value of Example E-10 was greater than that of Reference Examples R-7-1. Furthermore, referring to Reference Examples R-7-2 and Example E-10 in Table 11, Example E-10 included both the first component and the third component, and Reference Examples R-7-2 only included the third component. As shown in Table 11, the γ1/K11 value of Example E-10 was smaller than that of Reference Examples R-7-2, Accordingly, by using both the first component and the third component, the Δε value was maintained in a specific range, and the γ1/K11 value may be significantly reduced. Therefore, the response speed of the liquid crystal composition may be effectively increased.

As mentioned above, the disclosure provides a liquid crystal compound having high dielectric anisotropy (Δε), high refractive anisotropy (Δn), improved rotational viscosity coefficient (γ1), improved ratio of rotational viscosity coefficient to dielectric anisotropy (γ1/Δε), and improved response speed. Furthermore, the disclosure also provides a liquid crystal composition. The liquid crystal composition has reduced rotational viscosity coefficient (γ1<60), increased elastic coefficient (K11>9), and reduced γ1/K11 value (γ1/K11<5.5), while maintaining the Δε value at a sufficiently high value (Δε>5). In addition, the Δε, γ1, K11, and γ1/K11 value can be tailored to a desired range by adjusting the choosing compound and the corresponding content of the first, third, and fourth components. Therefore, the display using the liquid crystal composition of the disclosure may have higher response speed and lower energy consumption, and the afterimage issue may be improved.

Although the disclosure has been described by way of example and in terms of the preferred embodiments, it should be understood that various modifications and similar arrangements (as would be apparent to those skilled in the art) can be made herein without departing from the spirit and scope of the disclosure as defined by the appended claims.

What is claimed is:

1. A liquid crystal composition, comprising: a first component and a third component; wherein
the first component comprises at least two liquid crystal compounds represented by Formula (I)

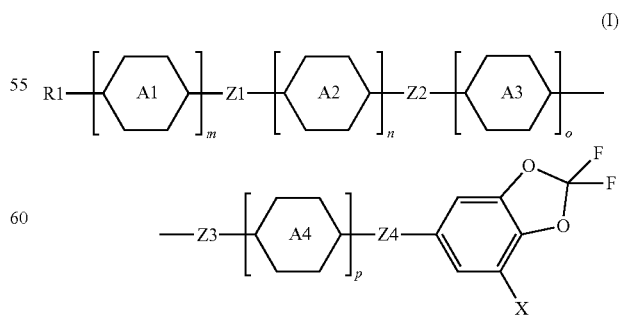

wherein
R1 represents hydrogen, a $C_1$-$C_{10}$ alkyl group, or a $C_2$-$C_{10}$ alkenyl group, where the $C_1$-$C_{10}$ alkyl group or the $C_2$-$C_{10}$ alkenyl group is unsubstituted or at least one —$CH_2$— of the $C_1$-$C_{10}$ alkyl group or the $C_2$-$C_{10}$ alkenyl group is replaced by —O—, —S—, —O—CO—, —OC—O—, or —O—CO—O—, provided that the —O—, —S—, —O—CO—, —OC—O—, and —O—CO—O— do not directly bond to one another, and/or at least one hydrogen of the $C_1$-$C_{10}$ alkyl group or the $C_2$-$C_{10}$ alkenyl group is substituted by halogen, CN, or $CF_3$;

each of A1, A2, A3, and A4 independently represents a 1,4-phenylene group, a 1,4-cyclohexylene group, a divalent dioxabicyclo[2.2.2]octylene group, a divalent trioxabicyclo[2.2.2]octylene group, or a divalent 2,5-indanylene group, where the 1,4-phenylene group, the 1,4-cyclohexylene group, or the divalent 2,5-indanylene group is unsubstituted or at least one hydrogen of the 1,4-phenylene group, the 1,4-cyclohexylene group, or the divalent 2,5-indanylene group is substituted by halogen, CN, or $CF_3$, and/or at least one —$CH_2$— of the 1,4-cyclohexylene group is replaced by —O—, —S—, —O—CO—, —OC—O—, or —O—CO—O—, provided that the —O—, —S—, —O—CO—, —OC—O—, and —O—CO—O— do not directly bond to one another, and/or at least one —$CH_2$— of the divalent 2,5-indanylene group is replaced by —O— or —S—, provided that the —O— and —S— do not directly bond to one another;

each of Z1, Z2, Z3 and Z4 independently represents a single bond, a C1-C4 alkylene group, a C2-C4 alkenylene group, a $C_2$-$C_4$ alkynylene group, —O—CO—, or —CO—O—, where the $C_1$-$C_4$ alkylene group, the $C_2$-$C_4$ alkenylene group, or the $C_2$-$C_4$ alkynylene group is unsubstituted or at least one hydrogen of the $C_1$-$C_4$ alkylene group, the $C_2$-$C_4$ alkenylene group, or the $C_2$-$C_4$ alkynylene group is substituted by halogen, and/or at least one —$CH_2$— of the $C_1$-$C_4$ alkylene group, the $C_2$-$C_4$ alkenylene group, or the $C_2$-$C_4$ alkynylene group is replaced by —O— or —S—, provided that the —O— and —S— do not directly bond to each other, wherein at least one of Z1, Z2, Z3, and Z4 of one of the at least two liquid crystal compounds does not represent —$OCF_2$— or —$CF_2O$—;

X represents hydrogen, halogen, CN, $CF_3$, or $CCl_3$; and each of m, n, o, and p independently represents 0 or 1, and m+n+o+p>0;

the third component comprises at least one liquid crystal compound represented by Formula (III)

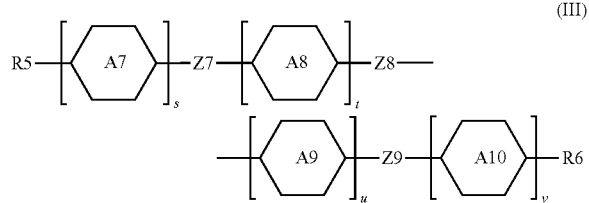

(III)

wherein

R6 represents halogen, —$CF_3$, —OCH=$CF_2$, or —$OCF_3$;

R5 represents hydrogen, a $C_1$-$C_{10}$ alkyl group, or a $C_2$-$C_{10}$ alkenyl group, where the $C_1$-$C_{10}$ alkyl group or the $C_2$-$C_{10}$ alkenyl group is unsubstituted or at least one —$CH_2$— of the $C_1$-$C_{10}$ alkyl group or the $C_2$-$C_{10}$ alkenyl group is replaced by —O—, —S—, —CO—, —O—CO—, —CO—O—, or —O—CO—O—, and wherein the —O—, —S—, —CO—, —O—CO—, —CO—O—, and —O—CO—O— do not directly bond to one another, and/or at least one hydrogen of the $C_1$-$C_{10}$ alkyl group or the $C_2$-$C_{10}$ alkenyl group is substituted by halogen, CN, or $CF_3$;

each of A7, A8, A9, and A10 independently represents a 1,4-phenylene group, a 1,4-cyclohexylene group, a divalent dioxabicyclo[2.2.2]octylene group, a divalent trioxabicyclo[2.2.2]octylene group, or a divalent 2,5-indanylene group, where the 1,4-phenylene group, the 1,4-cyclohexylene group, or the divalent 2,5-indanylene group is unsubstituted or at least one hydrogen of the 1,4-phenylene group, the 1,4-cyclohexylene group, or the divalent 2,5-indanylene group is substituted by halogen or CN, and/or at least one —$CH_2$— of the 1,4-cyclohexylene group is replaced by —O—, —NH—, or —S—, provided that the —O—, —NH—, and —S— do not directly bond to one another, or at least one —$CH_2$— of the divalent 2,5-indanylene group is replaced by —O—, —NH—, or —S—, provided that the —O—, —NH—, and —S— do not directly bond to one another;

each of Z7, Z8 and Z9 independently represents a single bond, a $C_1$-$C_4$ alkylene group, a $C_2$-$C_4$ alkenylene group, a $C_2$-$C_4$ alkynylene group, —CO—O—, or —O—CO—, where the $C_1$-$C_4$ alkylene group, the C2-C4 alkenylene group, or the $C_2$-$C_4$ alkynylene group is unsubstituted or at least one hydrogen of the $C_1$-$C_4$ alkylene group, the $C_2$-$C_4$ alkenylene group, or the $C_2$-$C_4$ alkynylene group is substituted by halogen, and/or at least one —$CH_2$— of the $C_1$-$C_4$ alkylene group, the $C_2$-$C_4$ alkenylene group, or the $C_2$-$C_4$ alkynylene group is replaced by —O— or —S—, and —O— does not directly bond to —O— or —S—, and —S— does not directly bond to —S—, and wherein at least one of Z7, Z8 and Z9 represents —$OCF_2$— or —$CF_2O$—; and each of s, t, u, and v independently represents 0, 1, 2, or 3, and s+t+u+v≥3.

2. The liquid crystal composition as claimed in claim 1, wherein at least one of A1, A2, A3, and A4 of one of the at least two liquid crystal compounds represents the 1,4-phenylene group or the 1,4-cyclohexylene group, and at least one hydrogen of the 1,4-phenylene group or the 1,4-cyclohexylene group is substituted by halogen, CN, or $CF_3$.

3. The liquid crystal composition as claimed in claim 1, wherein at least one of A1, A2, and A3 of one of the at least two liquid crystal compounds represents

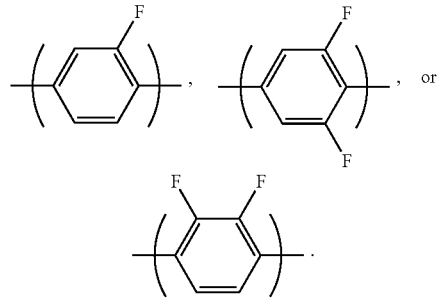

4. The liquid crystal composition as claimed in claim 1, wherein at least one of A1, A2, and A3 of one of the at least two liquid crystal compounds represents

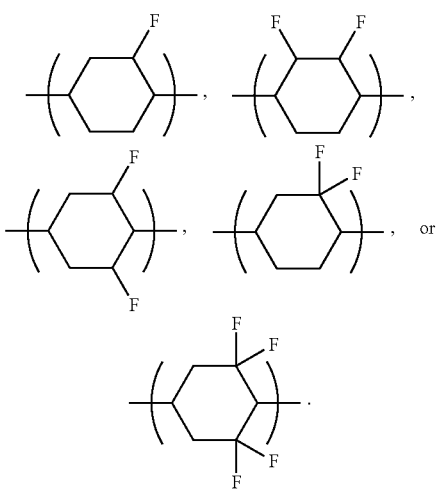

5. The liquid crystal composition as claimed in claim 2, wherein at least one of m, n, o, and p of one of the at least two liquid crystal compounds is 0.

6. The liquid crystal composition as claimed in claim 1, wherein X of one of the at least two liquid crystal compounds represents fluorine.

7. The liquid crystal composition as claimed in claim 1, further comprising:
a second component comprising at least one liquid crystal compound represented by Formula (II)

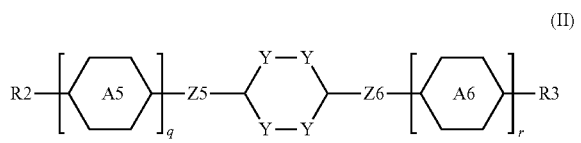

(II)

wherein
R3 represents a $C_1$-$C_{10}$ alkyl group, a $C_2$-$C_{10}$ alkenyl group, halogen, —$CF_3$, —OCH=$CF_2$, or —$OCF_3$;
R2 represents hydrogen, a $C_1$-$C_{10}$ alkyl group, or a $C_2$-$C_{10}$ alkenyl group, where the $C_1$-$C_{10}$ alkyl group or the $C_2$-$C_{10}$ alkenyl group is unsubstituted or at least one —$CH_2$— of the $C_1$-$C_{10}$ alkyl group or the $C_2$-$C_{10}$ alkenyl group is replaced by —O—, —S—, —CO—, —O—CO—, —CO—O—, or —O—CO—O—, and wherein the —O—, —S—, —CO—, —O—CO—, —CO—O—, and —O—CO—O— do not directly bond to one another, and/or at least one hydrogen of the $C_1$-$C_{10}$ alkyl group or the $C_2$-$C_{10}$ alkenyl group is substituted by halogen, CN, or $CF_3$;
Y represents —C(R4)$_2$—, —O—, or —S—, and —O— does not directly bond to —O— or —S—, and —S— does not directly bond to —S—, where each of R4 independently represents hydrogen or halogen;
each of A5 and A6 independently represents a 1,4-phenylene group, a 1,4-cyclohexylene group, a divalent dioxabicyclo[2.2.2]octylene group, a divalent trioxabicyclo[2.2.2]octylene group, or a divalent 2,5-indanylene group, where the 1,4-phenylene group, the 1,4-cyclohexylene group, or the divalent 2,5-indanylene group is unsubstituted or at least one hydrogen of the 1,4-phenylene group, the 1,4-cyclohexylene group, or the divalent 2,5-indanylene group is substituted by halogen or CN, and/or at least one —$CH_2$— of the 1,4-cyclohexylene group is replaced by —O—, —NH—, or —S—, provided that the —O—, —NH—, and —S— do not directly bond to one another, or at least one —$CH_2$— of the divalent 2,5-indanylene group is replaced by —O—, —NH—, or —S—, provided that the —O—, —NH—, and —S— do not directly bond to one another;
each of Z5 and Z6 independently represents a single bond, a C1-C4 alkylene group, a C2-C4 alkenylene group, a $C_2$-$C_4$ alkynylene group, —CO—O—, or —O—CO—, where the C1-C4 alkylene group, the C2-C4 alkenylene group, or the $C_2$-$C_4$ alkynylene group is unsubstituted or at least one hydrogen of the C1-C4 alkylene group, the C2-C4 alkenylene group, or the $C_2$-$C_4$ alkynylene group is substituted by halogen, and/or at least one —$CH_2$— of the C1-C4 alkylene group, the C2-C4 alkenylene group, or the $C_2$-$C_4$ alkynylene group is replaced by —O— or —S—, provided that the —O— and —S— do not directly bond to each other;
X represents hydrogen, halogen, CN, $CF_3$, or $CCl_3$; and
each of q and r independently represents 0, 1, or 2, and q+r≥1.

8. The liquid crystal composition as claimed in claim 7, wherein the liquid crystal compound represented by Formula (I) is 0.1-50 wt %, and the liquid crystal compound represented by Formula (II) is 10-99 wt %, based on a total weight of the liquid crystal composition.

9. The liquid crystal composition as claimed in claim 1, wherein Z4 of one of the at least two liquid crystal compounds represents —$OCF_2$— or —$CF_2O$—.

10. The liquid crystal composition as claimed in claim 1, wherein the third component comprises a liquid crystal compound represented by Formula (III), and at least one of A7, A8, A9, and A10 represents the divalent dioxabicyclo[2.2.2]octylene group, the divalent trioxabicyclo[2.2.2]octylene group, or the divalent 2,5-indanylene group, and wherein the divalent 2,5-indanylene group is unsubstituted or at least one hydrogen of the divalent 2,5-indanylene group is substituted by fluorine, and/or at least one —$CH_2$— of the divalent 2,5-indanylene group is replaced by —O—, provided that the —O— does not directly bond to —O—.

11. The liquid crystal composition as claimed in claim 1, wherein the third component comprises a liquid crystal compound represented by Formula (III), and at least one of A7, A8, A9, and A10 represents the 1,4-phenylene group, wherein the 1,4-phenylene group is unsubstituted or at least one hydrogen of the 1,4-phenylene group is substituted by fluorine.

12. The liquid crystal composition as claimed in claim 1, further comprising:
a fourth component comprising at least one liquid crystal compound represented by Formula (IV)

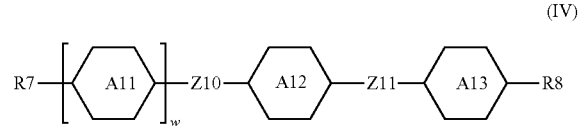

(IV)

wherein
each of R7 and R8 independently represents a $C_1$-$C_{15}$ alkyl group or a $C_2$-$C_{15}$ alkenyl group, wherein at least one —$CH_2$— of the $C_1$-$C_{15}$ alkyl group or the $C_2$-$C_{15}$ alkenyl group is replaced by —O—, and wherein —O— does not directly bond to —O—;

each of A11, A12, and A13 independently represents a 1,4-phenylene group, a 1,4-cyclohexylene group, or a 2,5-tetrahydropyranyl group, wherein the 1,4-phenylene group, the 1,4-cyclohexylene group, or the 2,5-tetrahydropyranyl group is unsubstituted or at least one hydrogen of the 1,4-phenylene group, the 1,4-cyclohexylene group, or the 2,5-tetrahydropyranyl group is substituted by fluorine;

each of Z10 and Z11 independently represents a single bond, a C1-C4 alkylene group, a C2-C4 alkenylene group, a $C_2$-$C_4$ alkynylene group, —CO—O—, or —O—CO—, wherein the C1-C4 alkylene group, the C2-C4 alkenylene group, or the $C_2$-$C_4$ alkynylene group is unsubstituted or at least one hydrogen of the C1-C4 alkylene group, the C2-C4 alkenylene group, or the $C_2$-$C_4$ alkynylene group is substituted by halogen or CN, and/or at least one —CH$_2$— of the C1-C4 alkylene group, the C2-C4 alkenylene group, or the $C_2$-$C_4$ alkynylene group is replaced by —O— or —S—, and —O— does not directly bond to —O— or —S—, and —S— does not directly bond to —S—; and w represents an integer greater than or equal to 0.

13. The liquid crystal composition as claimed in claim 12, wherein the first component is 1-45 wt %, the third component is 1-45 wt %, and the fourth component is 10-70 wt %, based on a total weight of the liquid crystal composition.

14. The liquid crystal composition as claimed in claim 13, wherein a total content of the first component and the third component is 5-50 wt %, based on a total weight of the liquid crystal composition.

15. The liquid crystal composition as claimed in claim 2, wherein at least one of A2, A3, and A4 of one of the at least two liquid crystal compounds represents the 1,4-phenylene group, and at least one hydrogen of the 1,4-phenylene group is substituted by halogen.

16. The liquid crystal composition as claimed in claim 1, wherein at least one of Z3 and Z4 of one of the at least two liquid crystal compounds represents —CF$_2$O— or —OCF$_2$—.

* * * * *